US010632298B2

(12) United States Patent
Butterfield et al.

(10) Patent No.: US 10,632,298 B2
(45) Date of Patent: Apr. 28, 2020

(54) FLUID INFUSION SYSTEMS AND METHODS

(71) Applicant: CareFusion 303, Inc., San Diego, CA (US)

(72) Inventors: Robert Dwaine Butterfield, Poway, CA (US); Scott Hellen, San Diego, CA (US); Vaclav Barina, Middletown, NY (US); Allison Leigh Barry, San Jose, CA (US); Julie Chang, Walnut, CA (US); Jeanette M. Liu, Monterey Park, CA (US); Huy Quang Nguyen, Winnetka, CA (US); Michelle Wei, Arcadia, CA (US); Samuel A. Derose, San Diego, CA (US); Thendral Govindaraj, San Diego, CA (US); Samantha Hoang, San Diego, CA (US); Andrew L. Marino, San Diego, CA (US); Raul Sun Han Chang, San Diego, CA (US); Arthur Y. Chang, San Diego, CA (US); Deval Gupta, San Diego, CA (US)

(73) Assignee: CareFusion 303, Inc., San Diego, CA (US)

( * ) Notice: Subject to any disclaimer, the term of this patent is extended or adjusted under 35 U.S.C. 154(b) by 458 days.

(21) Appl. No.: 15/405,213

(22) Filed: Jan. 12, 2017

(65) Prior Publication Data

US 2017/0120035 A1 May 4, 2017

Related U.S. Application Data

(63) Continuation of application No. PCT/US2016/030236, filed on Apr. 29, 2016.

(Continued)

(51) Int. Cl.
*A61M 39/22* (2006.01)
*A61M 5/14* (2006.01)
*A61M 39/28* (2006.01)

(52) U.S. Cl.
CPC ........ *A61M 39/227* (2013.01); *A61M 5/1409* (2013.01); *A61M 39/284* (2013.01); *A61M 39/281* (2013.01)

(58) Field of Classification Search
CPC .............. A61M 39/227; A61M 39/284; A61M 5/1409; A61M 39/281
See application file for complete search history.

(56) References Cited

U.S. PATENT DOCUMENTS

2013/0331789 A1* 12/2013 Butterfield .......... A61M 5/1408 604/151
2014/0060655 A1* 3/2014 Ramos .................... F16K 7/063 137/1

FOREIGN PATENT DOCUMENTS

| EP | 1541184 A1 | 6/2005 |
|----|------------|--------|
| EP | 2965771 A1 | 1/2016 |
| WO | WO-2013188461 A1 | 12/2013 |

OTHER PUBLICATIONS

International Search Report and Written Opinion for Application No. PCT/US2016/030236, dated Nov. 15, 2016, 17 pages.

* cited by examiner

*Primary Examiner* — Lauren P Farrar
(74) *Attorney, Agent, or Firm* — Morgan, Lewis & Bockius, LLP

(57) ABSTRACT

Systems and methods are disclosed for controlling the flow of fluids in a fluid infusion system. The system may include first and second fluid containers, first and second tubes coupled to the first and second fluid containers, and an external valve coupled to the second tube and configured to (Continued)

be attached to the first tube. The valve may be configured to shape the first tube to form a valve region which is opened or closed by an actuating element in the valve that is driven by hydrostatic pressure from the second tube. A full second container may generate a pressure that is concentrated through a diaphragm onto a pin which presses on the shaped first tube region, closing it to allow only fluid from the second container to flow. When the fluid level in the second line falls reducing pressure, the pin's force reduces until the first tube is opened.

7 Claims, 19 Drawing Sheets

Related U.S. Application Data

(60) Provisional application No. 62/156,739, filed on May 4, 2015, provisional application No. 62/292,810, filed on Feb. 8, 2016.

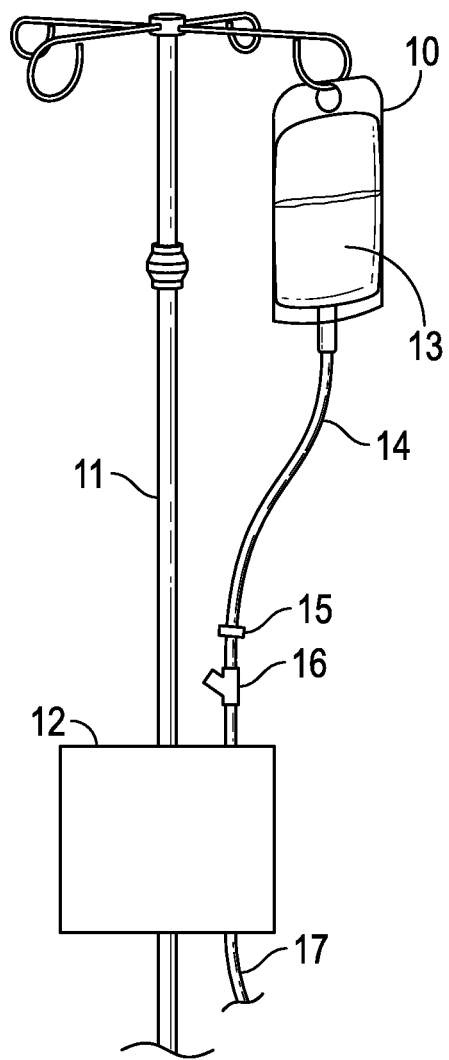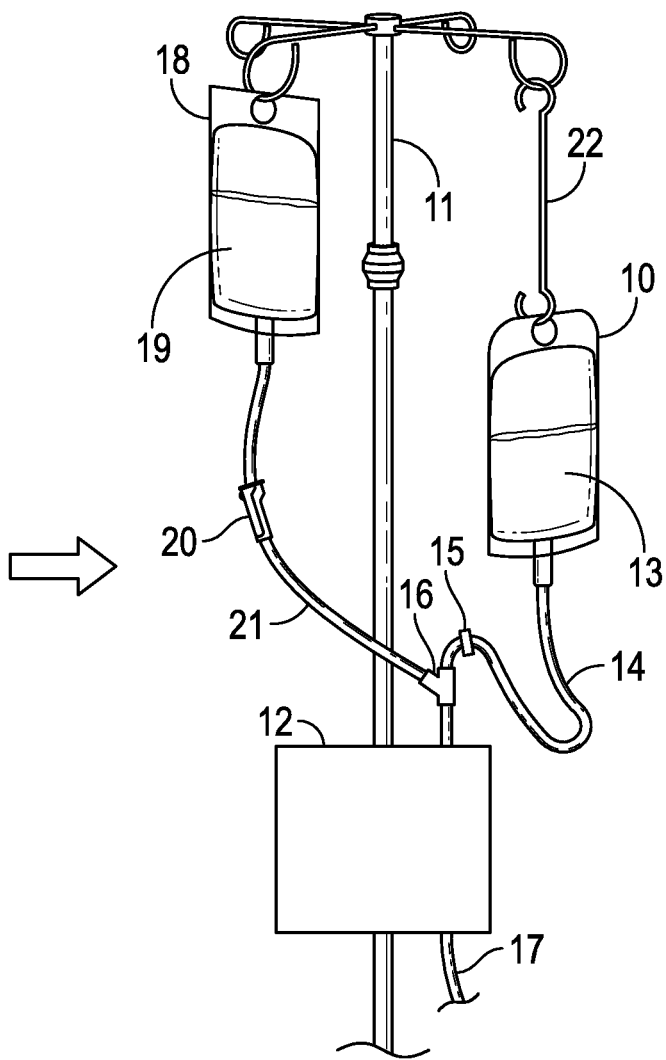
FIG. 1A  FIG. 1B

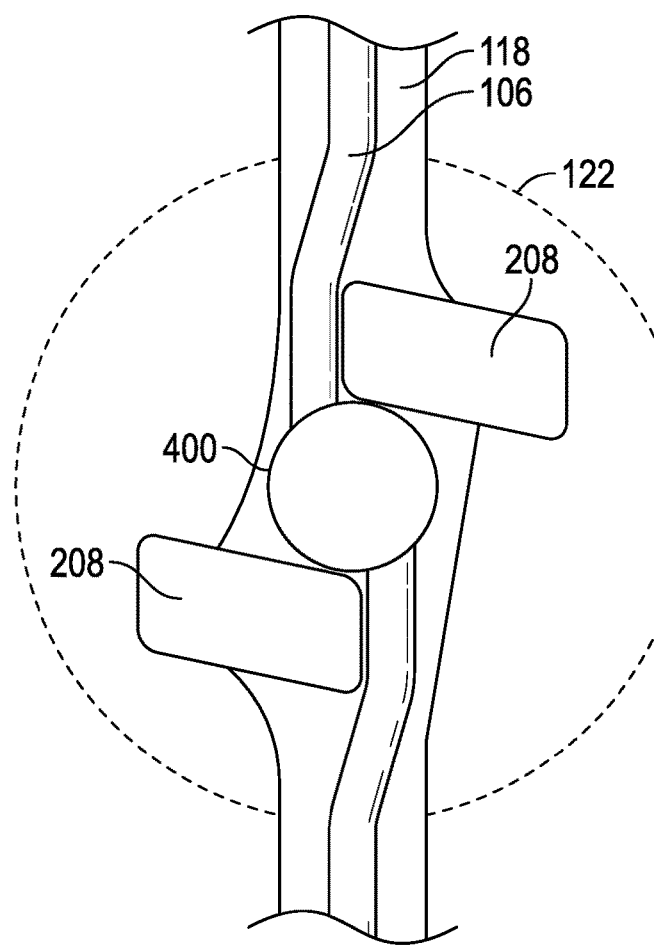
FIG. 5
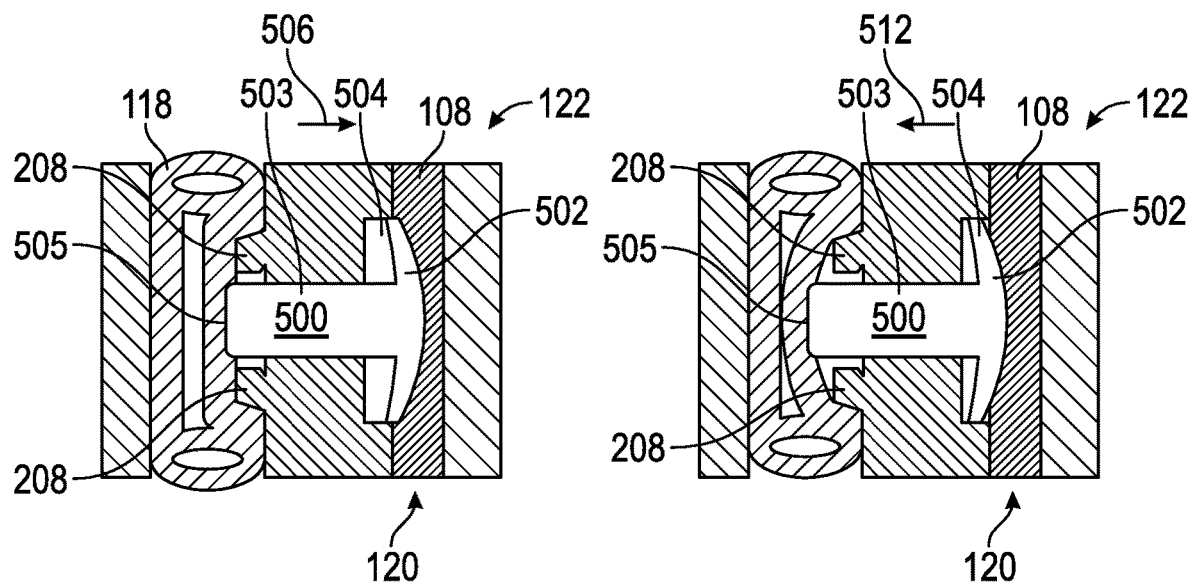
FIG. 6A  FIG. 6B

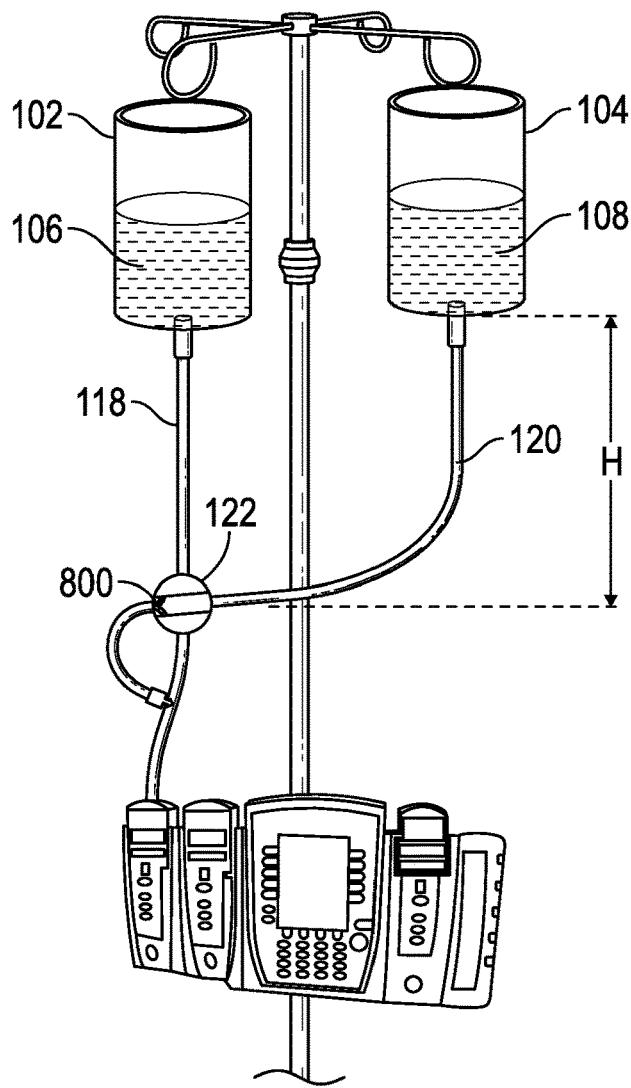
FIG. 12A
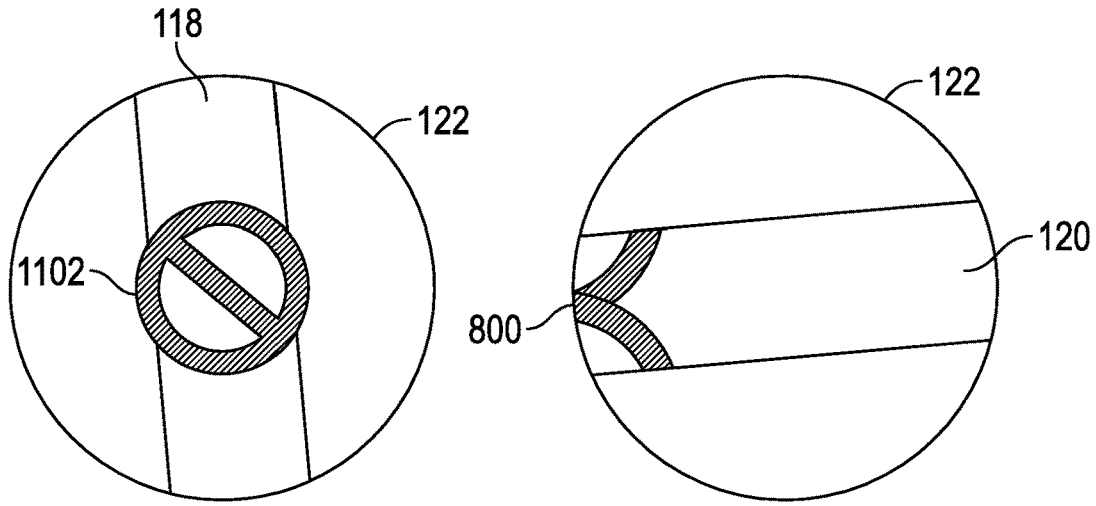
FIG. 12B  FIG. 12C

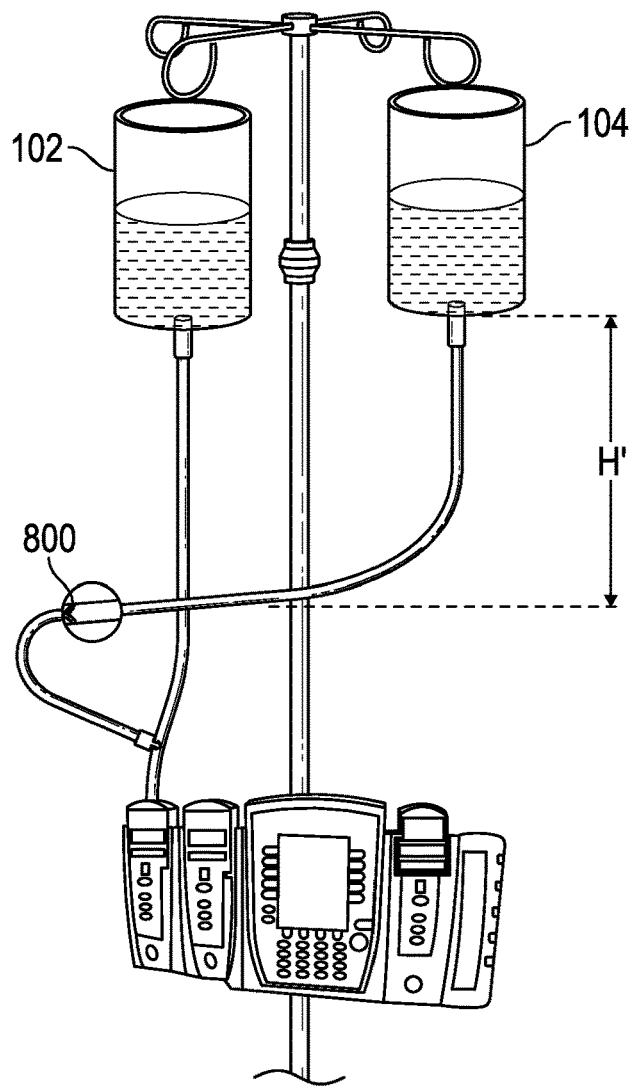
FIG. 13A
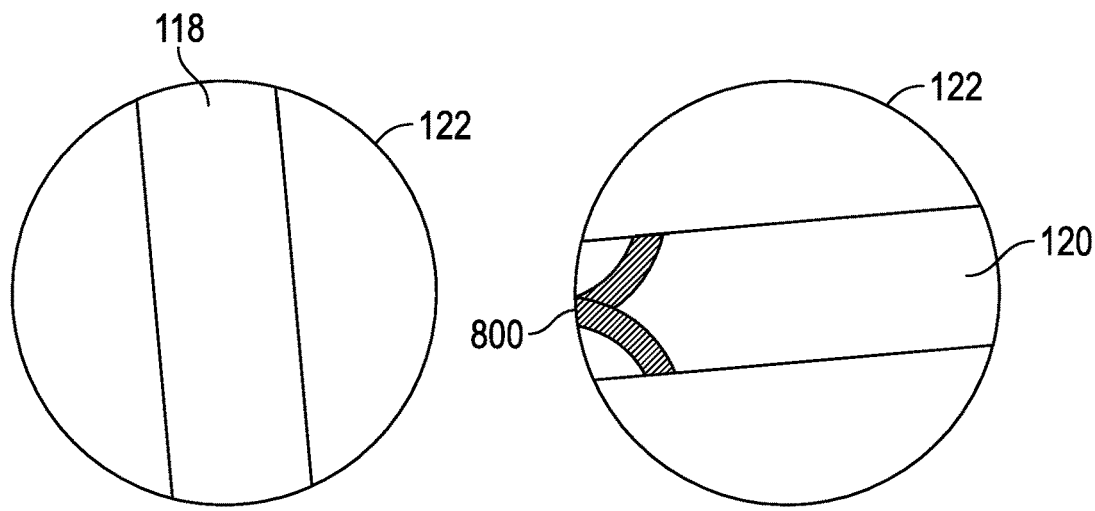
FIG. 13B  FIG. 13C

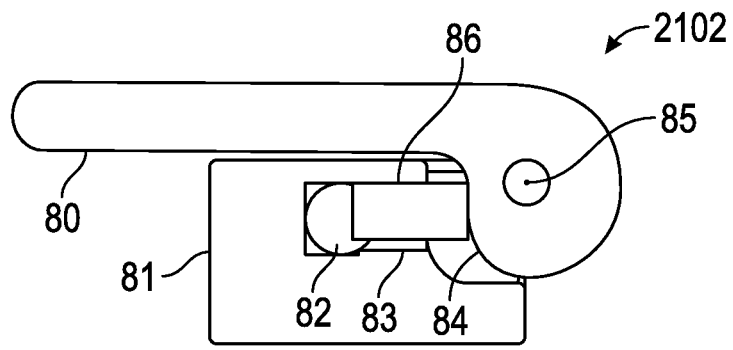
FIG. 19A
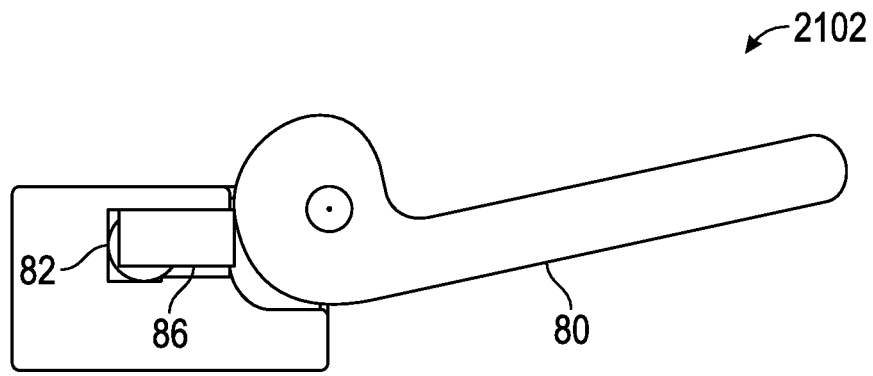
FIG. 19B
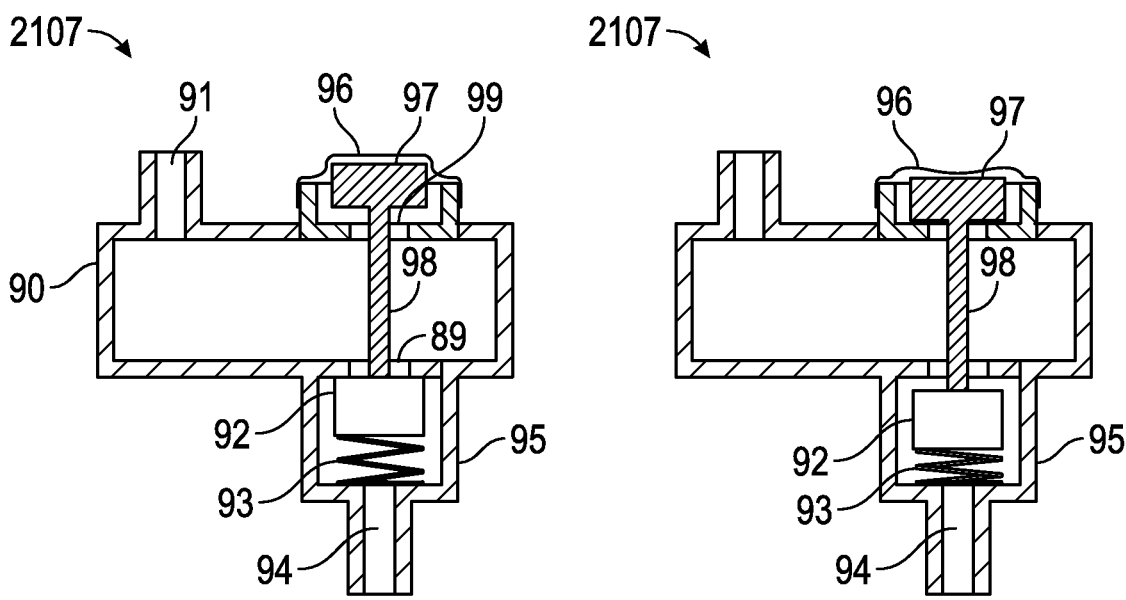
FIG. 20A  FIG. 20B

FLUID INFUSION SYSTEMS AND METHODS

CROSS-REFERENCE TO RELATED APPLICATIONS

This application is a continuation of International Patent Application No. PCT/US2016/030236, entitled "FLUID INFUSION SYSTEMS AND METHODS," filed on Apr. 29, 2016, which claims priority to and benefit of U.S. Provisional Patent Application No. 62/156,739, entitled "FLUID INFUSION SYSTEMS AND METHODS," filed on May 4, 2015, and U.S. Provisional Patent Application No. 62/292,810, entitled "SECONDARY FLUID INFUSION SYSTEMS AND METHODS," filed on Feb. 8, 2016, the entire contents of each of which are hereby incorporated by reference herein for all purposes.

BACKGROUND

Field

The present disclosure generally relates to the administration of medication by infusion and, more particularly, to systems and methods for delivering primary and secondary fluid infusions.

SUMMARY

Patients are routinely prescribed medical fluids or medications that are administered in a liquid form by infusion that is commonly accomplished using an infusion pump that delivers the medical fluid at a controlled rate. For example, intravenous (IV) infusions are used for introducing nutrients, medications, and other fluids directly into a patient's bloodstream, where, for example, they can be readily absorbed and circulated to facilitate recovery. In many cases, intermittent doses of secondary fluid medications such as antibiotics and chemotherapeutics are administered that must be combined or intermittently provided with other primary fluids and medications given before and after the secondary fluids and medications using the same pump and main infusion tubing line.

For example, secondary infusions can take advantage of an existing IV line (e.g., a primary line) that already has access to the patient's bloodstream. Typically, in secondary infusions, the primary line is used to supply nutrition or long delivery medications and the secondary line is used to provide intermittent or short-term medications. Although secondary infusions initially served as simply a more convenient way to administer small volume antibiotics, more recently these techniques have been employed in other applications, such as chemotherapy.

Many systems for delivering primary and secondary (intermittent) fluids introduce the intermittent medication into the IV pump tubing just upstream of the pump using a "needle-free" self-closing port by placing a secondary container containing a secondary fluid above a primary container containing the primary fluid to generate a pressure imbalance that closes a check valve on the primary fluid line to stop the flow of the primary fluid and allow the secondary fluid to be administered.

However, if care is not taken, these systems can suffer from a number of complications and vulnerabilities due, for example, to user error or equipment failure which may result in delayed or incomplete therapy, inefficiency in providing the therapy, and potential damage to portions of the system tubing. For example, a nurse or other administrator must remember which of the primary and secondary containers is to be lowered and by how much and an incorrect placement of the containers can result in delayed or incomplete delivery. For example, secondary infusions are often performed by a nurse such as a Registered Nurse. However, Registered Nurses (RNs) employed at large medical institutions can sometimes work long shifts treating a large number of patients over long hours. In these conditions, if care is not taken, RNs and other caregivers can become increasingly prone to mental lapses increasing the risk of error when performing multi-step tasks. As such, the administration of secondary infusions with conventional systems can be prone to mistakes, if care is not taken.

Accordingly, systems and methods are disclose that provide improved primary and secondary infusion systems that reduce the mental and physical burden on a caretaker to provide the secondary infusion.

Moreover, infusion systems that operable by a pressure imbalance that closes a check valve on the primary fluid line for a secondary infusion can, if the primary tubing with the check valve is never used for a secondary infusion, generate unnecessary and expensive waste since the check valve and other extra components may never be used, which can be economically undesirable.

The present disclosure generally relates to infusion systems and, in particular, an external valve configured to close a primary fluid line responsive to pressure from a secondary fluid line for infusion of primary and secondary fluids from respective primary and secondary containers disposed at a common height. The infusion systems and methods of the present disclosure provide precise delivery of primary and secondary fluids using fewer components and fewer user modifications to the system for providing the secondary fluid in comparison with conventional systems thus providing a more economical system and reducing the risk of human or system error.

More particularly, in accordance with an embodiment, the disclosed infusion system includes secondary tubing from a secondary container in which the secondary tubing includes a device such as an external valve configured to clamp onto the primary tubing from a primary container such that the device shapes the primary tubing to form a valve region which is opened or closed by an actuating element in the device. The actuating element may be configured to be actuated by hydrostatic pressure from the secondary tubing.

For example, when the secondary container is full, the pressure it exerts in the secondary tubing may be concentrated through a diaphragm of the actuating element onto a pin of the actuating element which presses on the shaped primary tubing region. The pressure of the pin may close the primary tubing, thereby preventing flow of the primary fluid and allowing only the secondary fluid to flow. When the secondary container is empty and the secondary fluid level falls, thus reducing pressure in the secondary tubing, the pin's force reduces until the primary tubing is opened.

In some embodiments, a one way valve is provided in the secondary tubing that is configured to prevent primary fluid from flowing backward into the secondary tubing as the primary fluid empties. The one way valve may be manually operated to be either held open for priming or held closed for handling fluid.

The check valve in the secondary tubing may also permit the pump to check for correct installation of the device on the primary fluid line. For example, the pump may reverse the flow of the primary fluid briefly and check for a change in the fluid pressure in the primary fluid line to determine whether the primary tubing has been closed by the device.

In certain embodiments, a valve is disclosed that includes first and second structures configured to be disposed on opposing sides of a first fluid line, where the first structure includes a recess configured to receive the first fluid line; at least one tab in the recess configured to partially compress the first fluid line; and an actuating mechanism configured to be moved toward the first fluid line by a pressure from a fluid within a second fluid line.

In certain embodiments, the at least one tab includes a first tab formed on a first side of the recess and a second tab formed on an opposing second side of the recess.

In certain embodiments, the first tab is disposed at a first location along the length of the recess and the second tab is disposed at a second, different, location along the length of the recess.

In certain embodiments, a system is disclosed that includes the valve and the second fluid line, where the valve is coupled to the second fluid line and the second fluid line includes a check valve.

In certain embodiments, the system further includes the first fluid line disposed in the recess; a first fluid container coupled to the first fluid line; a second fluid container coupled to the second fluid line; and a pump configured to receive fluids from the first and second fluid lines via the valve.

In certain embodiments, the first fluid container contains a first medical fluid and the second fluid container contains a second, different, medical fluid.

In certain embodiments, the actuating mechanism includes a diaphragm having a surface configured to contact the fluid in a portion of the second fluid line; and a pin extending from the diaphragm to the first fluid line, where the pin has a surface configured to contact a portion of the first fluid line, and where the diaphragm surface is larger than the pin surface.

In certain embodiments, a valve is disclosed that includes at least one structure having a recess configured to receive a first fluid line containing a first fluid; and an actuating mechanism configured to be moved toward the first fluid line by a pressure from a second fluid in a second fluid line, where the actuating mechanism includes: a diaphragm having a surface configured to contact the second fluid in a portion of the second fluid line; and a pin extending from the diaphragm to the first fluid line, where the pin has a surface configured to contact a portion of the first fluid line, and where the surface of the diaphragm is larger than the surface of the pin.

In certain embodiments the pressure from the second fluid in the second fluid line is generated by a hydrostatic pressure on the diaphragm from the second fluid in the second fluid line when a first fluid container coupled to the first fluid line is disposed at a common height with a second fluid container coupled to the second fluid line.

In certain embodiments, the first fluid container includes a first intravenous fluid bag containing a first medical fluid and the second fluid container includes a second intravenous fluid bag containing a second, different, medical fluid.

In certain embodiments, the valve further includes a plurality of protrusions in the recess configured to crimp the first fluid line.

In certain embodiments, a portion of the first fluid line that is crimped is disposed at least partially between first and second protrusions of the plurality of protrusions.

In certain embodiments, the at least one structure includes first and second structures configured to be snapped onto the first fluid line.

In certain embodiments, a system is disclosed that includes the valve and further includes a support structure; first and second containers attached at a common height to the support structure; first and second drip chambers coupled respectively between the first and second containers and the first and second fluid lines; a check valve in the second fluid line; and a pump configured to receive a first fluid from the first fluid line or a second fluid from second fluid line based on a position of the actuating mechanism of the valve.

In certain embodiments, a method is disclosed that includes providing a first fluid container coupled to a first fluid line; providing a second fluid container coupled to a second fluid line having an external valve with an actuating member; attaching the external valve to the first fluid line; and closing the first fluid line by moving the actuating member in a first direction using a hydrostatic pressure of a fluid in the second fluid line.

In certain embodiments, providing the first fluid container and providing the second fluid container include providing the first and second fluid containers at a common height above the external valve.

In certain embodiments, the method further includes opening the first fluid line by moving the actuating member in an opposing second direction using a hydrostatic pressure in the first fluid line when the hydrostatic pressure of the fluid in the second fluid line falls due to emptying of the second fluid container.

In certain embodiments, the method further includes opening a check valve in the second fluid line to back prime the second fluid line.

In certain embodiments, attaching the external valve to the first fluid line includes crimping the first fluid line by partially compressing portions of the first fluid line with a plurality of tabs disposed in a recess in the external valve.

In certain embodiments, a method of testing a medical fluid infusion system is disclosed, the method including: coupling a first fluid tube to an infusion pump; coupling a second fluid tube having a check valve to the infusion pump; attaching an external valve of the second fluid tube to the first fluid tube; attaching a first container coupled to the first fluid tube to a support structure at a height above the external valve; attaching a second container coupled to the second fluid tube to the support structure at the same height above the external valve; reversing a flow of a first fluid in the first fluid tube with the infusion pump; and determining whether the external valve is properly attached to the first fluid tube by monitoring a pressure in the first fluid tube while reversing the flow.

In certain embodiments, a portion of the external valve forms a portion of the second fluid tube, and the portion of the external valve includes a diaphragm of an actuating member of the external valve that is disposed in contact with a fluid in the second fluid tube.

In some embodiments, a valve is provided that functions to halt primary fluid flow in the presence of a secondary line connected to the same IV pump. A diaphragm may be provided in the valve that transmits hydrostatic pressure from fluid in the secondary fluid line to a wedge or other structure that pinches off the primary line during the secondary infusion. In these embodiments, once the secondary fluid has been depleted at or near the end of the secondary infusion, the wedge releases the primary line due to the lack of hydrostatic pressure in the secondary line, which allows primary fluid flow to resume. In some embodiments, a separate check valve may also be provided on the secondary line that prevents backflow of primary fluid into the secondary line when the secondary fluid level falls.

In various embodiments, additional features are provided, which are described in further detail hereinafter, that enable backpriming of the secondary line, which can be a critical preparation step for certain secondary infusions in some scenarios. For example, the valve may include valving structures for the secondary line such as a needle-free male Luer with a valve and a cap, a needle-free male Luer with a bypass, a priming valve, a lid valve, and/or a disengageable check valve in various combinations as described herein.

BRIEF DESCRIPTION OF THE DRAWINGS

The accompanying drawings, which are included to provide further understanding and are incorporated in and constitute a part of this specification, illustrate disclosed embodiments and together with the description serve to explain the principles of the disclosed embodiments. In the drawings:

FIGS. 1A and 1B show schematic diagrams of an infusion system for infusion of primary and secondary fluids, according to certain aspects of the disclosure.

FIG. 5 is a schematic cross-sectional top view of an external valve showing how tabs in the external valve may compress portions of a primary line, according to certain aspects of the disclosure.

FIG. 6A is a schematic cross-sectional side view of an external valve showing an actuating element of the external valve, according to certain aspects of the disclosure.

FIG. 6B is a schematic cross-sectional side view of the external valve showing how the actuating element of the external valve may be actuated by hydrostatic pressure in a secondary line to close a primary line, according to certain aspects of the disclosure.

FIGS. 12A-12C are schematics of the infusion system of FIG. 2 in a configuration in which the system detects a proper installation of the external valve on the primary line, according to certain aspects of the disclosure.

FIGS. 13A-13C are schematics of the infusion system of FIG. 2 in a configuration in which the system detects an improper installation of the external valve on the primary line, according to certain aspects of the disclosure.

FIG. 19A is a schematic cross-sectional side view of a lid valve for an external valve in which the lid valve is in an open position, according to certain aspects of the disclosure.

FIG. 19B is a schematic cross-sectional side view of a lid valve for an external valve in which the lid valve is in a closed position, according to certain aspects of the disclosure.

FIG. 20A is a schematic cross-sectional side view of a priming valve for an external valve in which the priming valve is in a closed position, according to certain aspects of the disclosure.

FIG. 20B is a schematic cross-sectional side view of a priming valve for an external valve in which the priming valve is in an open position, according to certain aspects of the disclosure.

DETAILED DESCRIPTION

Figure 2:
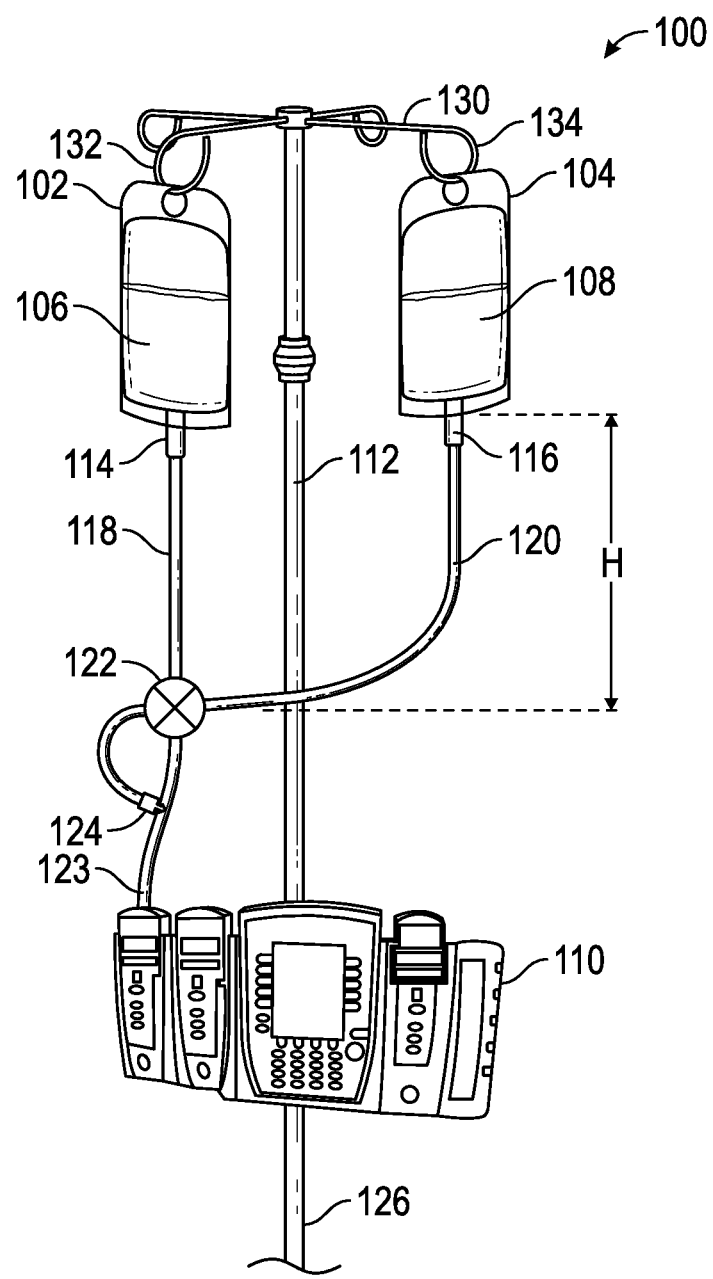
FIG. 2 is a schematic of an infusion system for infusion of primary and secondary fluids, according to certain aspects of the disclosure.

The embodiments of the methods and systems disclosed herein are presented in the context of an infusion system for the delivery of medical fluid to a patient. It will be apparent to those of ordinary skill in the art that the disclosed concepts may be applied to a variety of mechanisms for the pumping of liquids. Nothing in this disclosure should be interpreted, unless specifically stated as such, to limit the application of any method or system disclosed herein to medical applications and the disclosed concepts and methods may be applied to other fields that would also benefit from a secure method of distribution and dispensing. For example, food service systems that transfer liquids using a pump and tubing may use these same systems and methods.

Within this document, the term "medical fluid" comprises substances that are considered to be medications, particularly substances that are available only by a doctor's prescription, that may be provided in a liquid form as well as any other substance or mixture that may be used in a health-related treatment of a patient. Medical fluids include but are not limited to a saline solution or Ringer's lactate as well as active compounds such as an analgesic or an antimicrobial dispersed or dissolved within a carrier liquid.

In the following detailed description, numerous specific details are set forth to provide a full understanding of the present disclosure. It will be apparent, however, to one ordinarily skilled in the art that embodiments of the present disclosure may be practiced without some of the specific details. In other instances, well-known structures and techniques have not been shown in detail so as not to obscure the disclosure. In the referenced drawings, like numbered elements are the same or essentially similar.

FIG. 1A is a schematic diagram of an infusion system in a configuration for a primary infusion, according to certain aspects of the disclosure. As shown in FIG. 1A, primary drug container 10, which holds a primary fluid 13, is coupled for flow through a primary intravenous line 14 due to, for example, the pressure difference created by pump 12. The primary infusion configuration of FIG. 1A can be adjusted for a secondary infusion process as shown in FIG. 1B by lowering the primary drug container 10 using a suspension system or hanger 22 followed by the addition of a secondary drug container 18 coupled to a respective secondary line 21, which is connected to the primary line 14 via a mating junction or Y-site 16. The system of FIGS. 1A and 1B also includes a one-way valve or check valve 15 on the primary line 14 that impedes the secondary fluid 19 from flowing up into the primary line 14. Furthermore, the secondary line 21 includes a roller clamp 20 to occlude the flow of secondary fluid when necessary to allow for forward priming and backpriming.

As shown in FIG. 1B, the primary drug container 10 is lowered substantially (e.g., by a height in the range of 8" to 32") with respect to the height of the secondary drug container. Setting up a secondary infusion in this way includes a multistep process that includes spiking the secondary infusion container, priming the secondary line, connecting the secondary line to a Y-site on the primary line, lowering the primary fluid container with a hanger, and releasing a roller clamp on the secondary line to initiate fluid flow. However, to further reduce the number of steps to be performed by a caregiver (e.g., to prevent errors related to a caregiver forgetting to release the roller clamp 20 on the secondary line 21 or to lower the primary container 10 to the appropriate height), alternative embodiments are described hereinafter in connection with FIGS. 2-26.

In particular, as discussed in further detail hereinafter in connection with FIGS. 2-26, a secondary fluid line may be provided with a device such as external valve that can be mounted to the primary fluid line when delivery of a secondary fluid is desired. The secondary fluid may flow from a secondary container, through the external valve, into a lower portion of the primary fluid line (e.g., via a coupling mechanism such as a Y-site) into a pump for delivery to a patient. The secondary fluid may flow through the external valve when there is sufficient fluid in the secondary line to actuate an actuating mechanism (see, e.g., FIGS. 6A, 6B, and 16) in the external valve to close the primary fluid line. One aspect of secondary infusions is that, when the administration of secondary fluid is complete, primary fluid flow should resume. Thus, when there is insufficient pressure in the secondary line to close the primary fluid tube, the primary fluid may resume flow through the external valve to the lower portion of the primary fluid line and into the pump.

In some embodiments, the secondary fluid line may be provided with a one way valve such as a check valve to prevent flow of the primary fluid into the secondary fluid line and may be provided with one or more valving structures for priming the secondary fluid line. The valving structures may include various combinations discussed herein of a needle-free male Luer with a valve and a cap, a needle-free male Luer with a bypass, a priming valve, a lid valve, and/or a disengageable check valve such as an umbrella valve.

FIG. 2 is a schematic of an infusion system for infusion of primary and secondary fluids, according to certain aspects of the disclosure. As shown in FIG. 2, infusion system 100 may include a first container 102 (e.g., a primary fluid container) and a second container 104 (e.g., a secondary fluid container). First container 102 may contain a primary fluid 106 and provide the primary fluid 106 to a primary fluid line 118 (e.g., via a primary drip chamber 114). Secondary container 104 may contain a secondary fluid 108 and provide the secondary fluid 108 to a secondary fluid line 120 (e.g., via a secondary drip chamber 116). First and second containers 102 and 104 may, for example, be glass or plastic bottles or plastic bags such as intravenous fluid bags containing medical fluids.

Secondary fluid line 120 may be provided with a device such as external valve 122 that can be mounted to primary fluid line 118 when delivery of secondary fluid 108 is desired. Secondary fluid 108 may flow from secondary container 104 through external valve 122 into lower portion of the primary fluid line 123 (e.g., via a coupling mechanism 124) into a pump such as pump 110. Secondary fluid 108 may flow through external valve 122 when there is sufficient fluid in secondary line 120 to actuate an actuating mechanism (see, e.g., FIGS. 3-5) in external valve 122 to close primary fluid line 118. When there is insufficient pressure in secondary line 120 to close primary fluid tube 118, primary fluid 106 may flow through external valve 122 to lower portion of the primary fluid line 123 and into pump 110. In some embodiments, secondary fluid line 120 may be provided with a one way valve such as a check valve (see, e.g., FIG. 9A) to prevent flow of primary fluid 106 into secondary fluid line 120.

As shown in FIG. 2, primary container 102 and secondary container 104 may be disposed on a common support structure such as support structure 130 having one or more hangers such as hangers 132 and 134 that are supported at a common height (e.g., a common height above external valve 122) by an additional support structure such as pole 112. As described in further detail hereinafter, external valve 122 may be provided along with secondary fluid line 120 and configured to be installed onto the outside of primary fluid line 118. Pump 110 may be configured to pump an appropriate volume of secondary fluid 108 at an appropriate secondary flow rate so that at approximately the time the secondary container is empty, the pump 110 automatically transitions back to a main flow rate for providing primary fluid 106. Fluids 106 and 108 may be provided to a patient via downstream tubing 12.6 (e.g., an intravenous (IV) fluid line).

Figure 3:
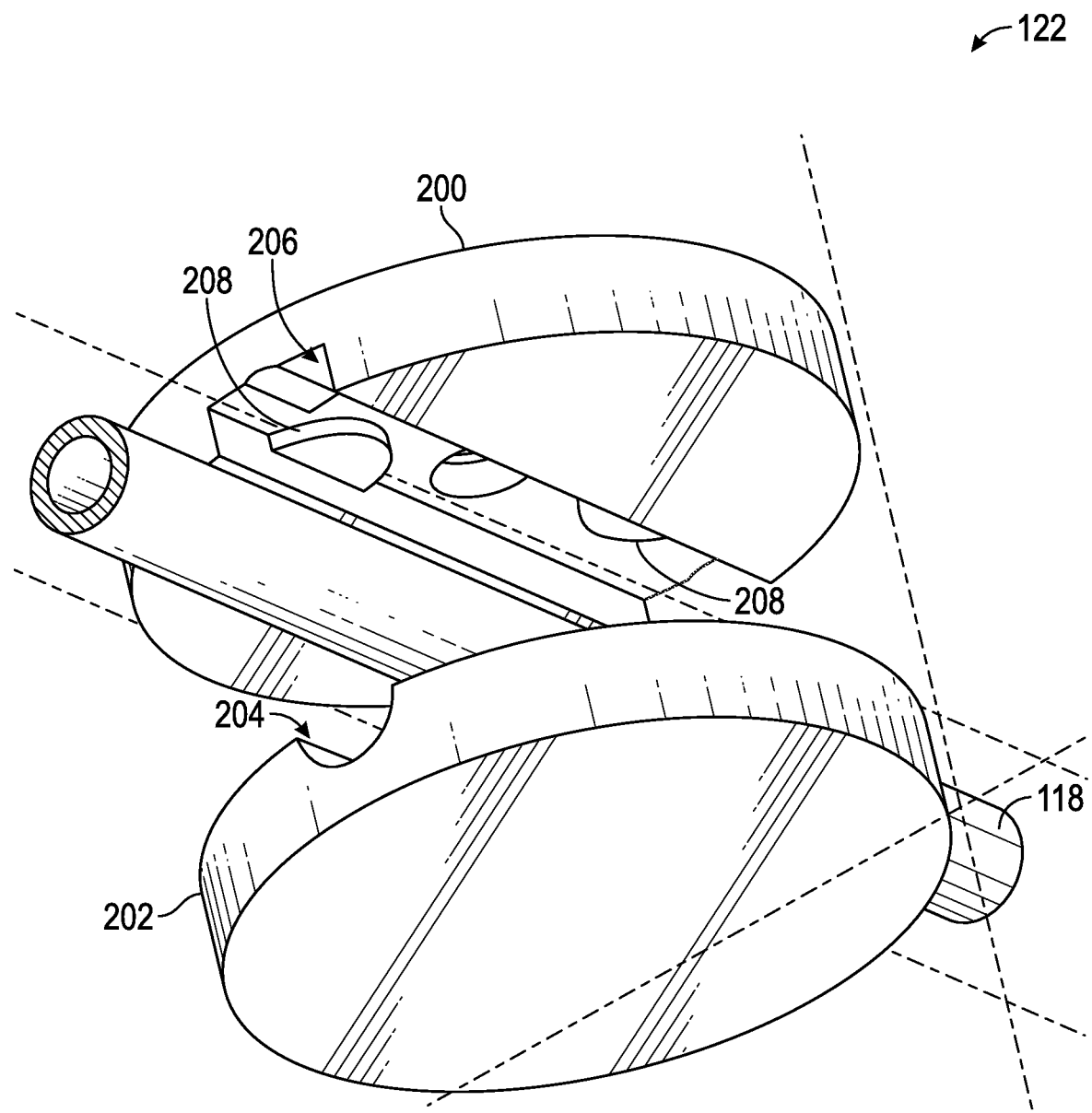
FIG. 3 is an exploded perspective view of an external valve, according to certain aspects of the disclosure.

FIG. 3 is an exploded perspective view of external valve 122, according to certain aspects of the disclosure. As shown in FIG. 3, external valve 122 may include a first structure 200 and a second structure 202 that are configured to be disposed on opposing sides of primary fluid line 118 such that primary fluid line 118 is disposed within a recess 204 in second structure 202 and a corresponding recess 206 in first structure 200. First and second structures 200 and 202 may include engagement mechanisms (not shown) that secure the structures together e.g., by snapping together the engagement structures) to secure external valve 122 onto the outside of primary fluid line 118. First and second structures 200 and 202 may be entirely separate structures that are engaged when pressed together or may have a permanent hinge-like attachment at one or more locations in order permit opening and closing around primary fluid line 118 similar to a clam shell.

Structure 200 may include one or more protrusions such as tabs 208 at various locations within recess 206. For example, as shown in FIG. 3, recess 206 may include a first tab 208 at a first location along the length of recess 206 and on a first side of recess 206 and may include a second tab 208 at a second, different location along the length of recess 206 and on an opposing side of recess 206 so that tabs 208 crimp the primary fluid line when structure 200 and structure 202 are pressed together onto primary fluid line 118.

Figure 4:
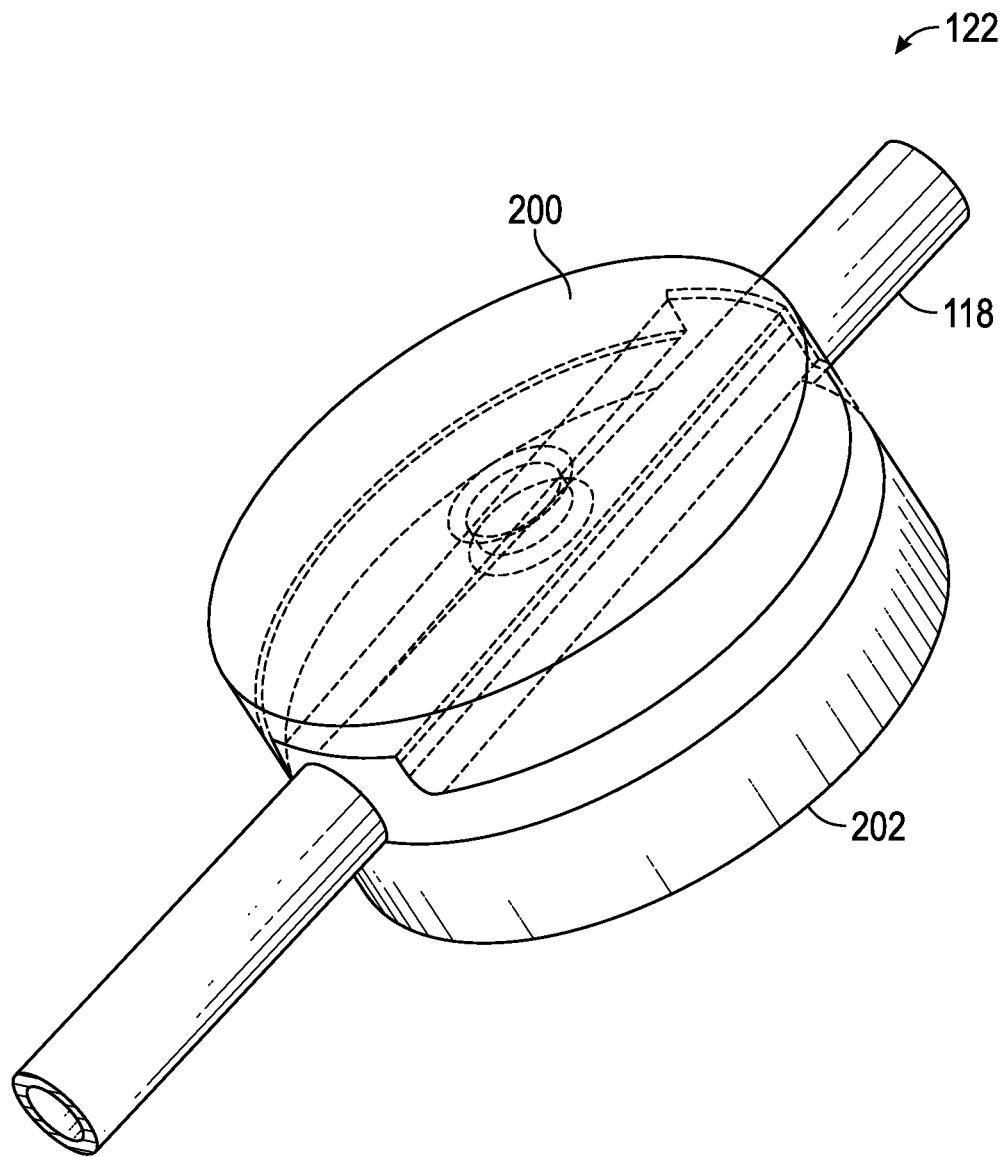
FIG. 4 is a perspective view of an external valve, according to certain aspects of the disclosure.

FIG. 4 is a perspective view of external valve 122 showing how structures 200 and 202 may be engaged together on primary fluid line 118, according to certain aspects of the disclosure. FIG. 5 is a schematic cross-sectional top view of external valve 122 showing how tabs 208 may be disposed on opposing sides and at different positions along the length of a recess in external valve 122 so that tabs 208 compress portions of primary fluid line 118 to crimp the primary fluid line, according to certain aspects of the disclosure. Pre-compression of the primary fluid line in this way reduces the pressure needed to compress the primary fluid line to shut off flow of the primary fluid 106. For example, in order to pinch a standard IV tube, a pressure of about 10 PSI is needed. However, in the configuration shown in FIG. 5 in which tabs 208 crimp the primary fluid line, a 10 PSI tube may be pinched with a pressure of only approximately 1 PSI. A pressure of approximately 1 PSI may be provided by hydrostatic pressure in the secondary tube that moves an actuating member in a valve such as valve 122, For example, structure 400 may be a diaphragm of an actuating member that can be pressed upon by a fluid in a secondary fluid tube to pinch the crimped portion of primary line 118 that is disposed between tabs 208.

FIG. 6A is a schematic cross-sectional side view of external valve 122 showing an actuating element 500 (sometimes referred to herein as an actuating member or actuating mechanism) of the external valve, according to certain aspects of the disclosure. As shown in FIG. 6A, an actuating element 500 may include a diaphragm 502 disposed in contact with secondary fluid 108 in secondary fluid line 120 and may include an extended portion 503 (e.g., a pin having a surface in contact with primary line 118 that is smaller than the surface of the diaphragm) that extends from the diaphragm into contact with an outer surface of primary fluid line 118 at a surface 505. The surface area of diaphragm 502 that has contact with the secondary fluid 108 in the secondary line 120 can be varied to ensure that sufficient pressure is provided to actuate the pin 503 in direction 512 toward primary line 118 to close primary line 118 as illustrated in FIG. 6B. When the pressure from secondary fluid 108 in secondary line 120 is reduced (e.g., when the secondary fluid container empties and the level of the secondary fluid falls to at or near the level of the external valve), pin 503 may be pushed back in direction 506 as there is insufficient pressure to close the primary fluid line 118 and thus resuming flow of primary fluid.

As shown in FIGS. 6A and 6B, a portion of secondary fluid line 120 may be formed from a portion of valve 122 such that secondary fluid 108 in that portion of secondary fluid line 120 is in contact with diaphragm 502 of actuating member 500.

Figure 7:
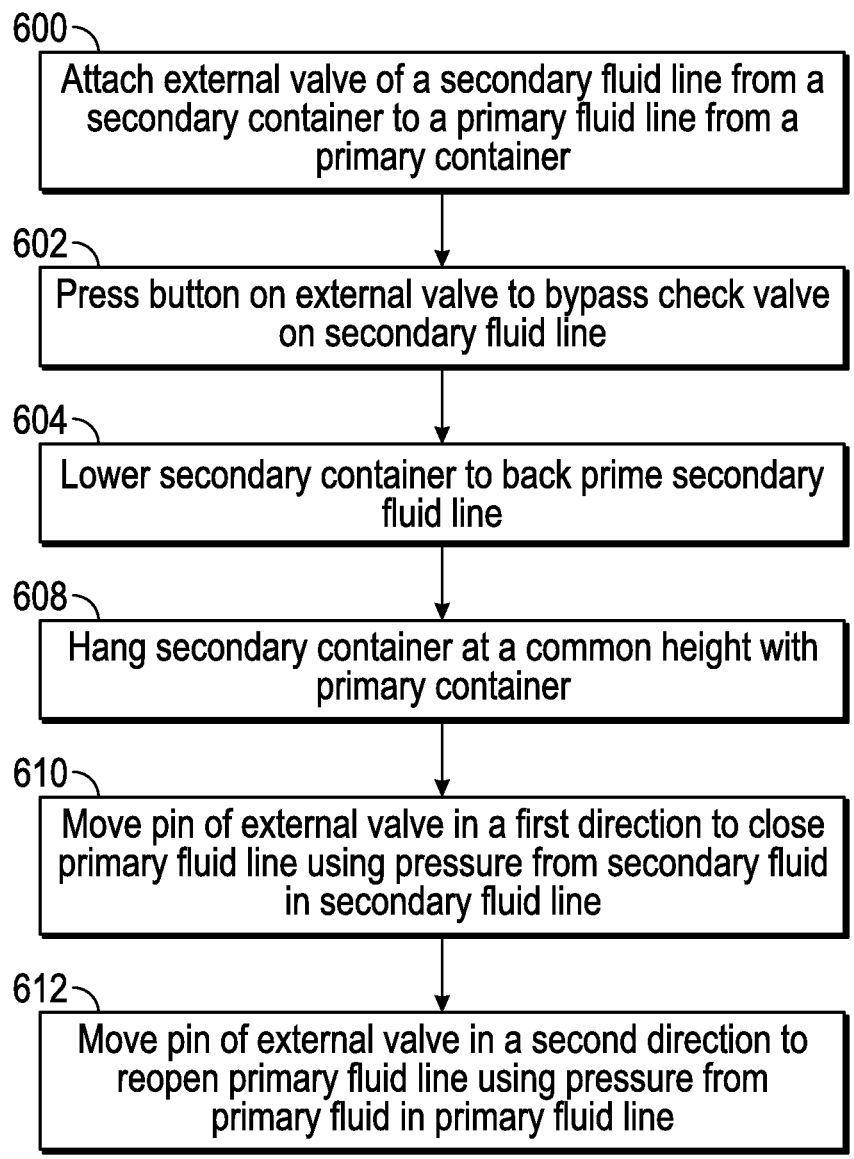
FIG. 7 is a flowchart of illustrative operations that may be performed for administering primary and secondary fluids using the system of FIG. 2, according to certain aspects of the disclosure.

FIG. 7 is a flowchart of illustrative operations that may be performed for administering primary and secondary fluids using the system of FIG. 2, according to certain aspects of the disclosure.

At step 600, an external valve such as external valve 122 of a secondary fluid line from a secondary container (e.g., secondary fluid line 120 from a secondary fluid container 104) may be attached to a primary fluid line from a primary container (e.g., to primary fluid line 118 from a primary fluid container 102). The external valve may be provided along with the secondary fluid line (e.g., the secondary fluid line may be provided with an external valve pre-installed) or the secondary fluid line may be coupled to the external valve before or after attaching the external valve to the primary fluid line. Attaching the external valve to the primary fluid line may include pressing opposing structures of the external valve together with the primary fluid line interposed between the structures so that tabs or other protrusions in a recess in one or both of the structures at least partially compresses portions of the primary fluid line (e.g., to crimp the primary fluid line).

In some situations, it may be desirable to back prime the secondary fluid line (e.g., if the secondary set has not already been pre-primed). In this type of scenario, optional steps 602 and 604 may be performed. At step 602, a button on the external valve may optionally be pressed to bypass (e.g., open) a check valve in the secondary fluid line. At step 604, the secondary container may optionally be lowered relative to the external valve to back prime secondary fluid line.

At step 606, the secondary container may be secured (e.g., hung) at a common height with primary container. For example, the secondary container may be hung from a common hanger structure with the primary container.

At step 608, a pin of the external valve may be moved (e.g., actuated in a first direction) to close the primary fluid line by pressure from the secondary fluid in the secondary fluid line. For example, the pin of the external valve may be moved when the secondary fluid in the secondary fluid line contacts and applies pressure on a diaphragm attached to the pin as described above in connection with FIGS. 6A and 6B.

At step 610, the pin of the external valve may be moved in a second, opposite, direction to reopen the primary fluid line by, for example, pressure from the primary fluid in the primary fluid line when the pressure from the secondary fluid on the diaphragm of the actuating member falls. The operations of steps 608 and 610 may occur automatically responsive to the pressures in the primary and secondary tubes when the external valve is attached to the primary fluid line and the secondary container and the primary container are disposed at substantially the same height (e.g., without any human operator action required).

Figure 8:
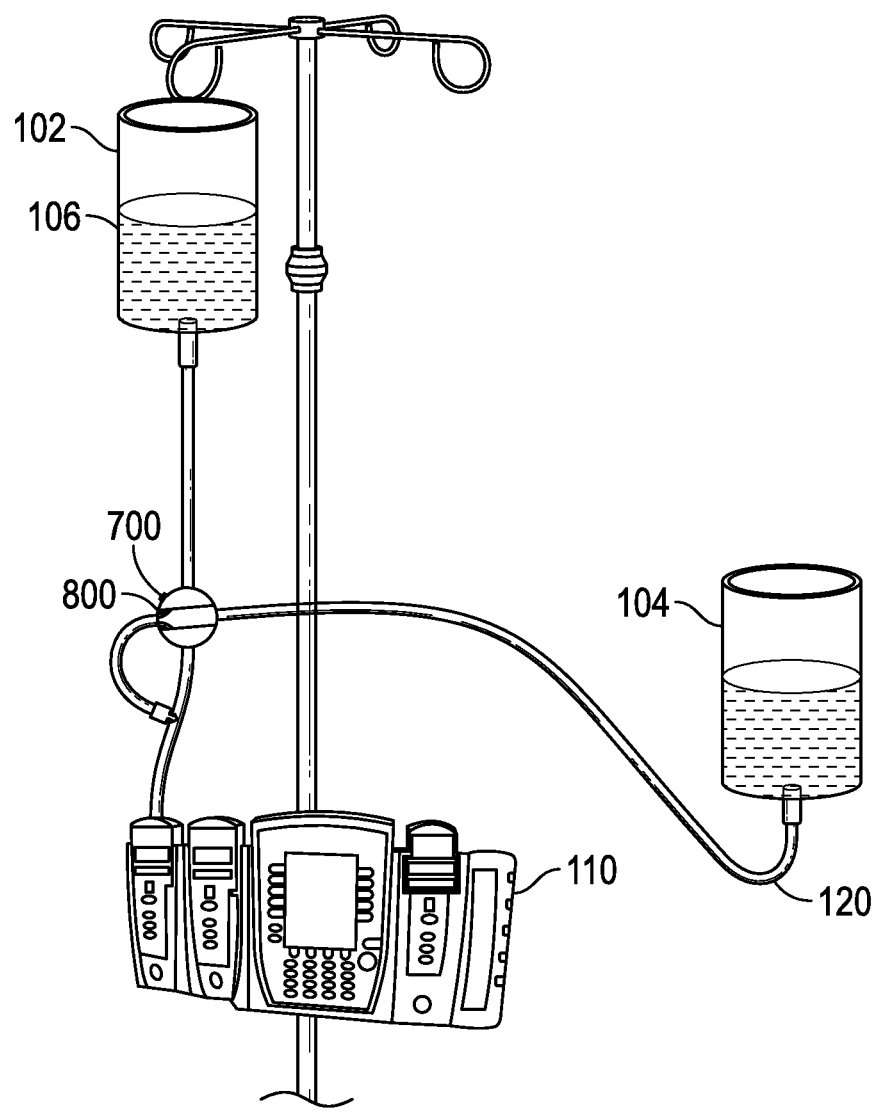
FIG. 8 is a schematic of an infusion system for infusion of primary and secondary fluids showing a mechanism for operating a check valve in a secondary tube to facilitate priming, according to certain aspects of the disclosure.

FIG. 8 is a schematic of an infusion system for infusion of primary and secondary fluids showing a mechanism 700 for operating a check valve 800 in secondary tube 120 to facilitate priming, according to certain aspects of the disclosure. Mechanism 700 (e.g., a button or switch that when manually operated) opens check valve 800 in secondary fluid line 120 so that primary fluid 106 can temporarily flow into secondary fluid line 120 to back prime the secondary set.

Figure 9A:
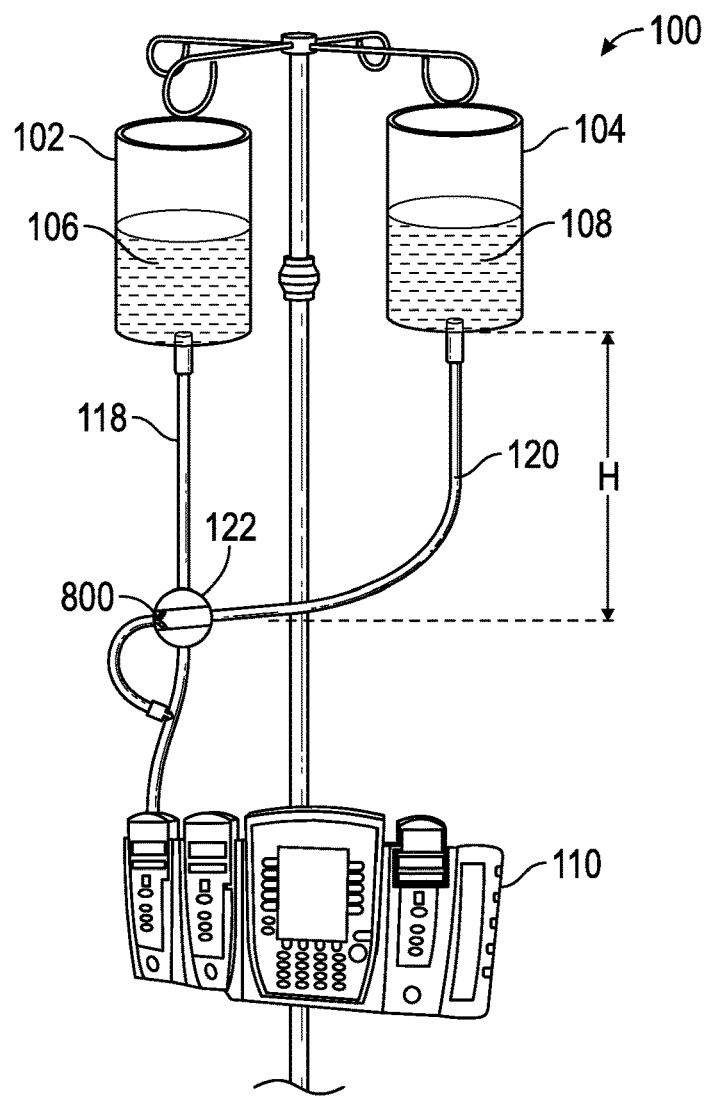
FIGS. 9A-9C are schematics of the infusion system of FIG. 2 in a configuration in which the primary line is closed by pressure in the secondary line for infusion of the secondary fluid in the secondary line, according to certain aspects of the disclosure.
Figure 9B:
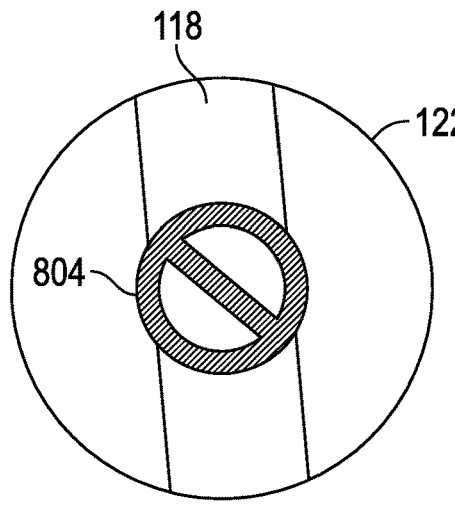
Figure 9C:
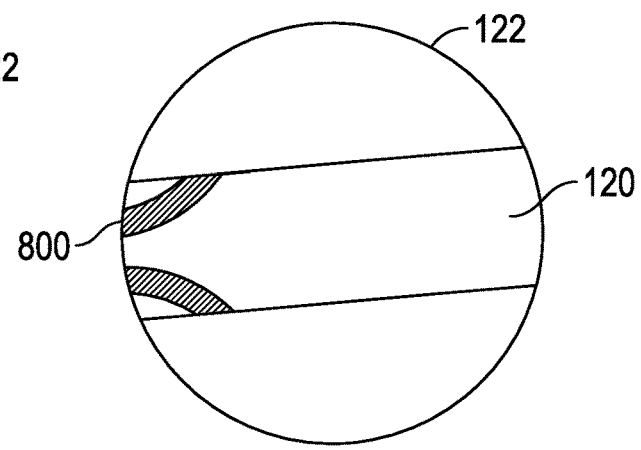

FIGS. 9A-9C are schematics of infusion system 100 of FIG. 2 in a configuration in which the primary line 118 is closed by pressure in the secondary line 120 for infusion of the secondary fluid 108 in the secondary line, according to certain aspects of the disclosure. As shown in FIG. 9A, a check valve 800 may be provided in the secondary fluid line 120. Check valve 800 may be configured to prevent back flow of primary fluid 106 into secondary fluid line 120 unless the check valve is manually opened as described above in connection with FIG. 8.

As shown in FIG. 9A, secondary container 104 may be secured (e.g., hung) at a height H (e.g., 24 inches) above the external valve 122 to provide sufficient hydrostatic pressure in secondary fluid line 120 to close primary fluid line 118 (as indicated by the closed symbol 804 in FIG. 9B) and to open check valve 800 (as shown in FIG. 9C) so that secondary fluid 108 only flows through external valve 122.

Figure 10A:
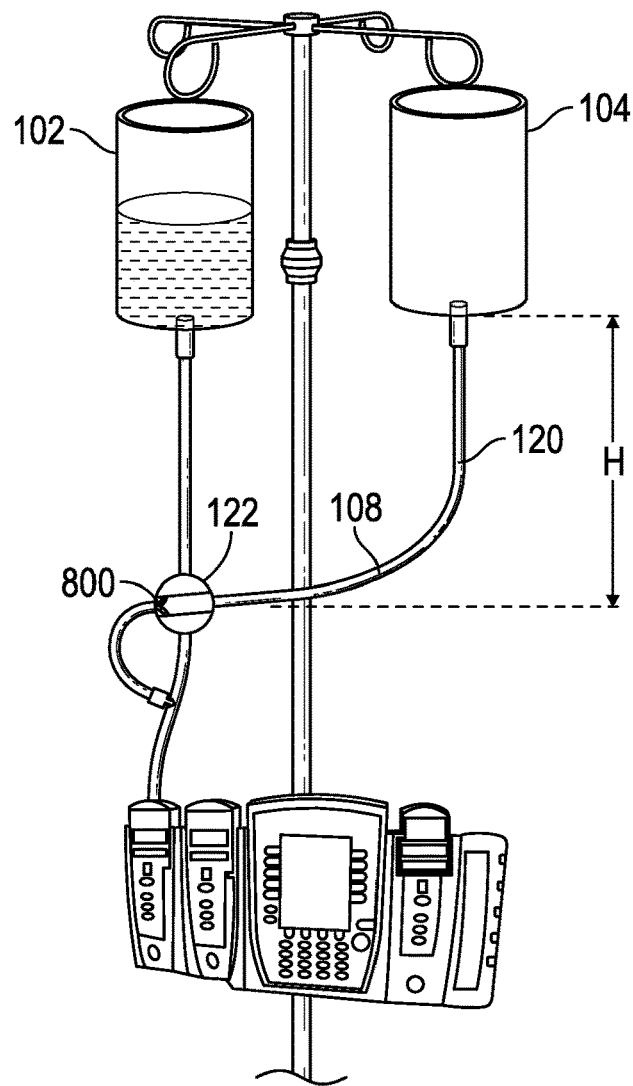
FIGS. 10A-10C are schematics of the infusion system of FIG. 2 in a configuration in which the secondary fluid has emptied and primary line is opened due to a lack of pressure in the secondary line for infusion of the primary fluid in the primary line, according to certain aspects of the disclosure.
Figure 10B:
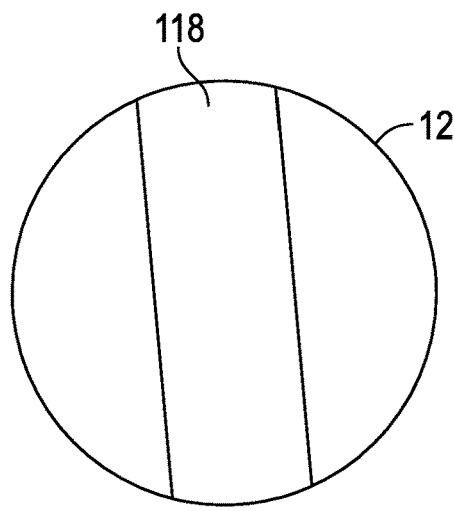
Figure 10C:
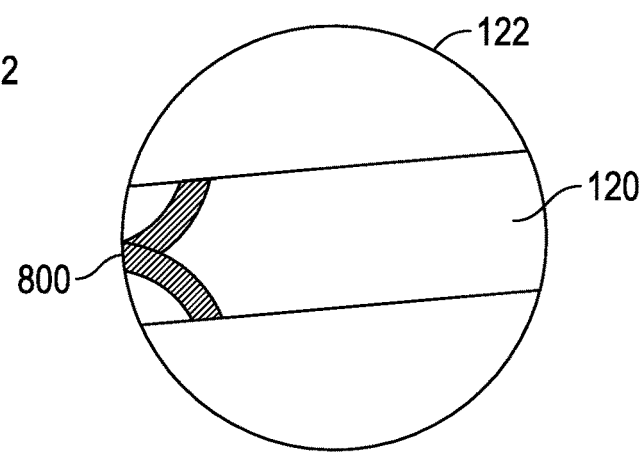

FIGS. 10A-10C are schematics of infusion system 100 of FIG. 2 in a configuration in which the primary line 118 is open due to a lack of pressure in the secondary line 120, according to certain aspects of the disclosure. As shown in the example of FIG. 10A, secondary fluid 108 may empty from secondary container 104 so that the level (height) of secondary fluid 108 falls to at or about the height of external valve 122. Pressure in secondary fluid line 120 may thus be reduced such that primary fluid line 118 is opened (as indicated in FIG. 10B) and check valve 800 is closed (as shown in FIG. 10C) thereby allowing primary fluid 106 to flow through external valve 122 without flowing into secondary fluid line 120.

It may be desirable to provide a test to ensure that external valve 122 is properly attached to primary fluid line 118 prior to administration of fluids from secondary fluid container 108 to prevent slow, delayed, or otherwise improper delivery of secondary fluid 108.

Figure 11:
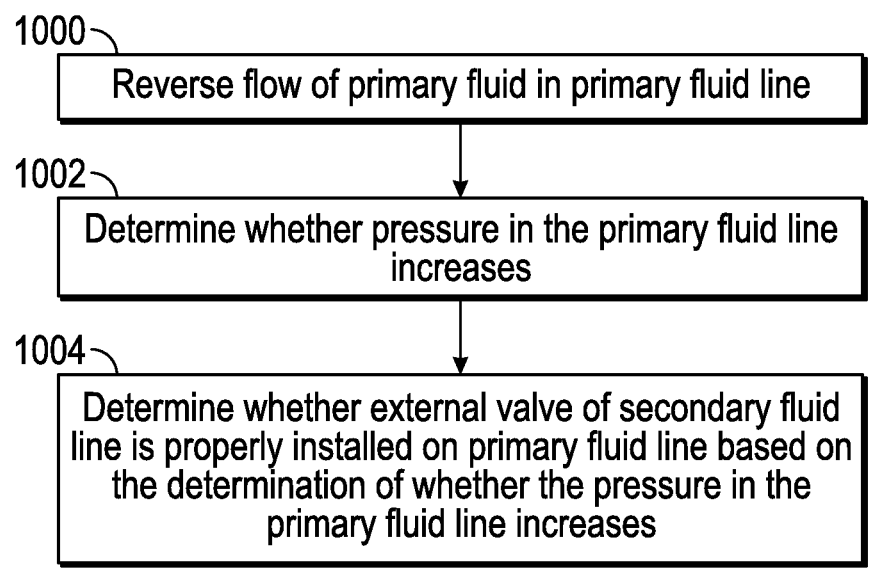
FIG. 11 is a flowchart of illustrative operations that may be performed for testing the system of FIG. 2, according to certain aspects of the disclosure.

FIG. 11 is a flowchart of illustrative operations that may be performed for testing infusion system 100 of FIG. 2, according to certain aspects of the disclosure.

At step 1000, the flow of a primary fluid in a primary fluid line may be reversed. For example, an IV pump controlling delivery of the primary fluid from the primary fluid line may reverse the flow of the primary fluid.

At step 1002, the pump or other system component may determine whether the pressure in the primary fluid line increases responsive to the reversal of the primary fluid flow.

At step 1004, the pump and/or another system component and/or an operator may determine whether the external valve of the secondary fluid line is properly installed on the primary fluid line based on the determination of whether the pressure in the primary fluid line increases. For example, if the external valve is properly installed and the secondary fluid container is disposed at the correct height, the primary fluid line should be closed by the external valve and the pressure in the primary fluid line should rise when the flow is reversed. Thus, if the pressure rises, the system may determine that the external valve is properly installed. Alternatively, if the pressure does not use (or does not use by an expected amount), the system may determine that the external valve is improperly installed. In some embodiments, if it is determined that the external valve may be improperly installed, an alarm or other alert may be provided to alert an operator that the external valve may be improperly installed.

FIGS. 12A-12C are schematics of infusion system 100 of FIG. 2 in a configuration in which the pump 110 detects or indicates a proper installation of the external valve 122 on the primary line 118, according to certain aspects of the disclosure. The flow of primary fluid 106 may be reversed to flow from the pump toward primary container 102. However, if external valve 122 is properly installed, primary fluid line 118 is closed as indicated by closed symbol 1102 of FIG. 12B and check valve 800 is also closed as indicated by FIG. 12C and no fluid can flow toward primary container 102. Thus, the pressure in primary fluid line 118 will rise indicating proper installation of external valve 122.

FIGS. 13A-13C are schematics of infusion system 100 of FIG. 2 in a configuration in which pump 110 detects an improper installation of the external valve 122 on the primary line 118 according to certain aspects of the disclosure. If external valve 122 is improperly installed (or if secondary container 104 is mounted at an improper high such as a height if), primary fluid line 118 is open as indicated by FIG. 13B and check valve 800 is closed as indicated by FIG. 13C and thus fluid 106 can flow toward primary container 102. Thus, the pressure in primary fluid line 118 will not rise indicating improper installation of external valve 122.

Figure 14C:
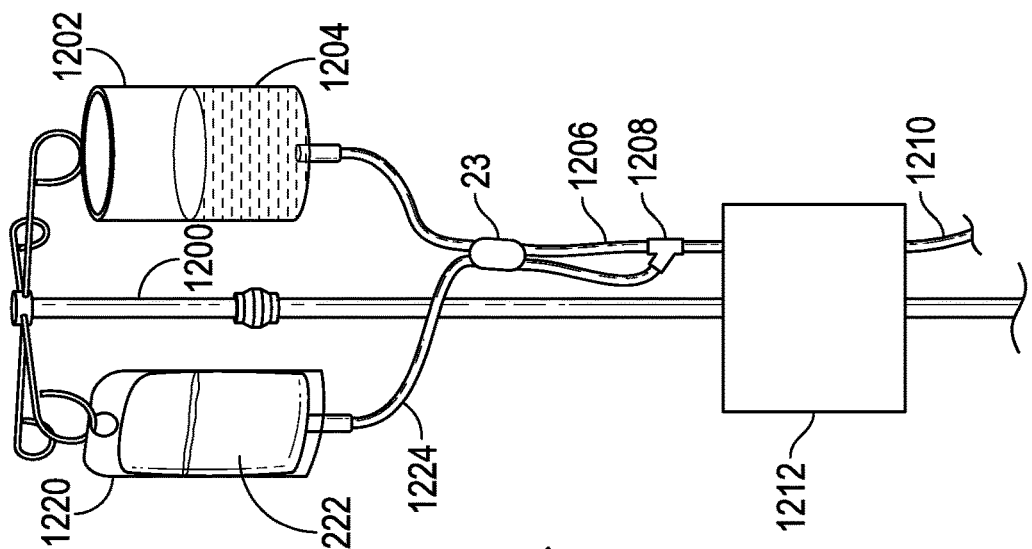
FIGS. 14A, 14B, and 14C show schematic diagrams of another infusion system for infusion of primary and secondary fluids, according to certain aspects of the disclosure.
Figure 14B:
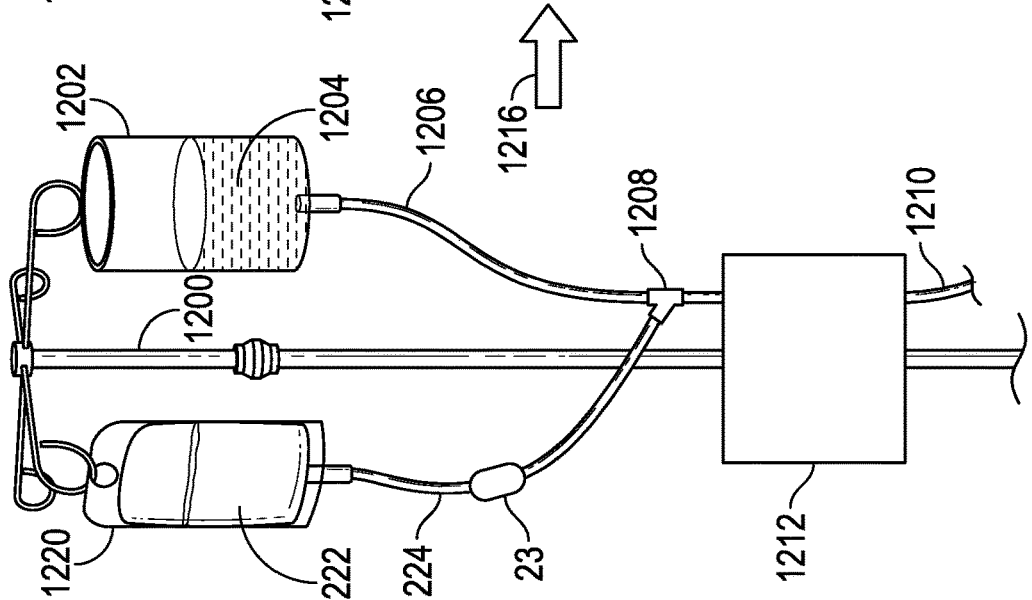
Figure 14A:
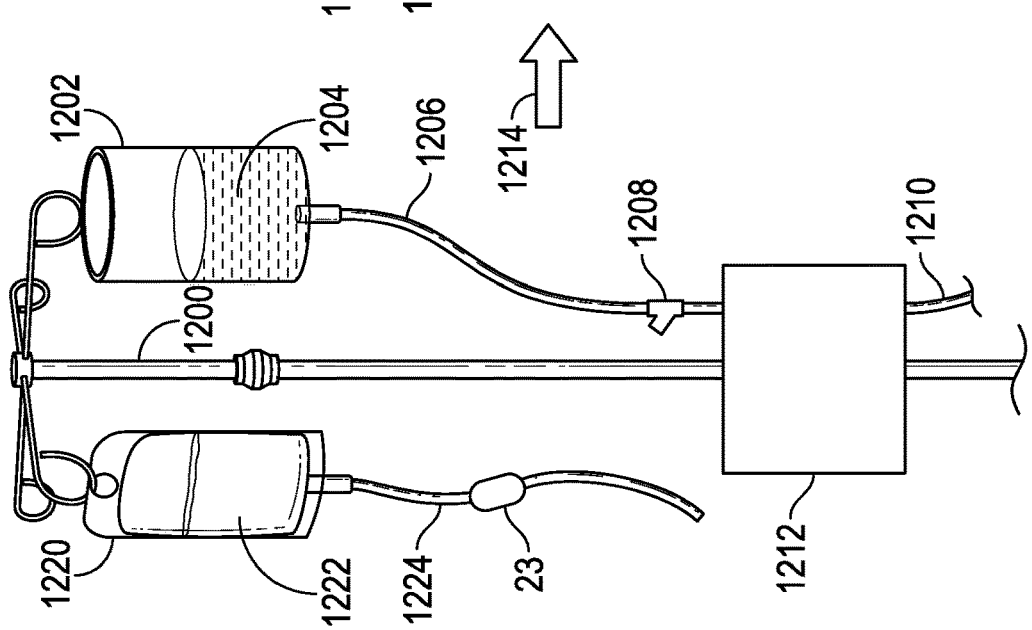

Referring now to FIG. 14A, a schematic diagram is shown of another infusion system in a configuration for a primary infusion and a secondary infusion, according to certain aspects of the disclosure. In the system of FIG. 14A, a primary fluid container 1202 containing a primary fluid 1204 is coupled to a primary line 1206 and is hung on an IV stand 1200. As shown, primary line 1206 includes a Y-site 1208 coupled between primary container 1202 and an infusion pump 1212. In IV infusion line 1210 is provided from the pump to provide pumped fluids to a patient.

FIG. 14A also shows a secondary infusion set that includes a secondary fluid container 1220 containing a secondary fluid 1222 and coupled to a secondary line 1224. As shown, an external valve 23 is attached to the secondary tubing 1224. External valve 23 may be embedded as part of the secondary line 1224. External valve may, for example, be an implementation of external valve 122 as described above in connection with FIGS. 2-13C and/or may include various features of external valves as described hereinafter in connection with FIGS. 14-26.

In order to couple the secondary infusion set to the primary infusion set for infusion of the secondary fluid, a caregiver may perform the operations of, spiking the secondary infusion container 1220, priming the secondary line 1224, connecting the secondary line 1224 to the Y-site 1208 on the primary line 1206 (see arrow 1214), and clamping the external valve 23 onto the primary line 1206 (arrow 1216).

FIG. 14B shows a configuration in which the end of the secondary line 1224 is coupled to the Y-site 1208. FIG. 14C shows the complete setup of the secondary intravenous infusion system in a configuration in which external valve 23 is clamped onto the primary line 1206.

Figure 15:
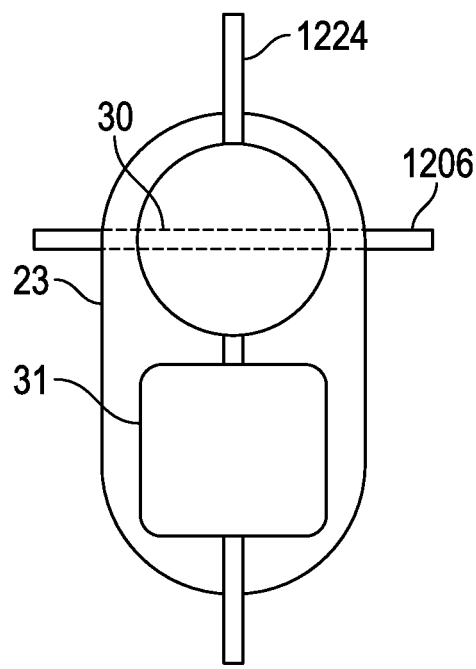
FIG. 15 is schematic diagram of an external valve, according to certain aspects of the disclosure.

Referring now to FIG. 15, a diagram of external valve 23 is shown, according to one or more embodiments. As shown in FIG. 15, external valve 23 may consist of a primary line valve 30 with the primary line 1206 secured therein, a secondary line valve 31, and the secondary line 1224.

Figure 16:
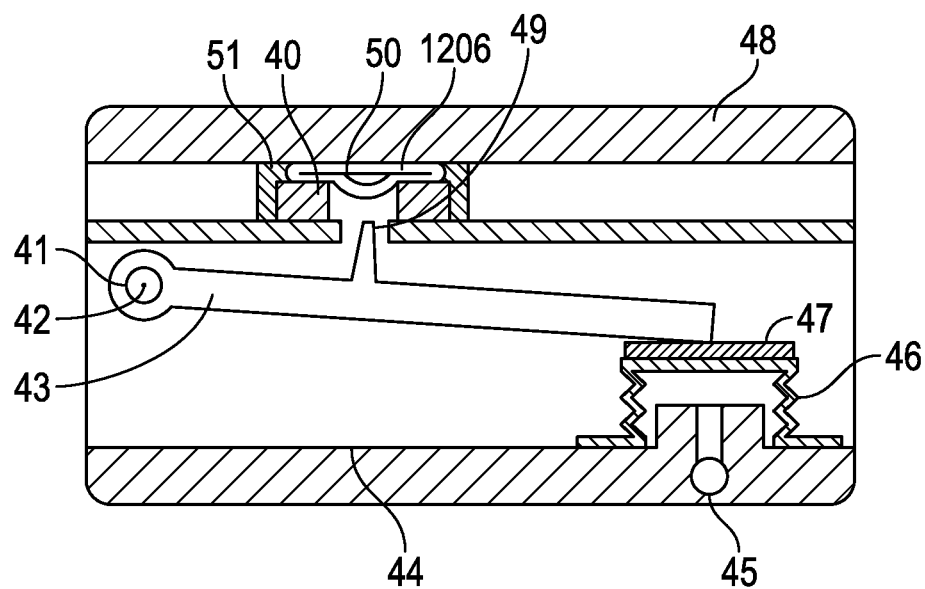
FIG. 16 is a schematic cross-sectional side view of a primary line valve of an external valve, according to certain aspects of the disclosure.

Referring now to FIG. 16, an embodiment of a primary line valve 30 is shown. In the example of FIG. 16, the primary line valve includes a housing 44 for an accordion-shaped diaphragm 46, a pusher plate 47 having a portion disposed in contact with (e.g., on top of) the diaphragm 46, an inlet/outlet port 45 for the secondary line 1224, a lever 43, a wedge 49, a sigma clamp 40, a rectangular cut-out 51 for the sigma clamp, and a lid 48. In the configuration of FIG. 16, the primary line 1206 is shown clamped inside the sigma clamp 40 by the closed lid 48. Lid 48 may be opened to release the primary line and/or for insertion of the primary line prior to clamping. As shown, in a closed configuration (e.g., when external valve 23 is clamped onto the primary line), the primary line may be at least partially compressed by sigma clamp 40 with a portion 50 remaining open for flow of the primary fluid therethrough in the absence of pressure from the secondary fluid. In this way, the pressure required to close the primary line by pinching portion 50 is reduced in comparison with the pressure that would be required to pinch the entire open primary line. Examples of arrangements for sigma clamp 40 are shown, for example, in FIGS. 3-5

Still referring to FIG. 16, primary line valve 30 is configured such that the hydrostatic pressure of the liquid 1222 in the secondary line 1224 (see, e.g., FIG. 14C) closes off the primary tubing. When the secondary fluid container 1220 (see, e.g., FIGS. 14A-14C) contains sufficient fluid, the fluid 1222 exerts a hydrostatic force on the diaphragm 46 proportional to its cross-sectional area. This diaphragm 46 interfaces with the top plate 47, and a bump on the pusher plate 47 pushes the lever 43. Correspondingly, the wedge 49 on the lever 43 pushes through the sigma clamp 40 to compress portion 50 and close the primary tubing 1206.

Still referring to FIG. 16, the sigma clamp 40 compresses the edges of portion 50. In addition, the wedge 49, before the liquid 1222 exerts a hydrostatic force on the diaphragm 46, pushes on the middle of the primary tubing 1206. These two characteristics together reduce the total displacement that the wedge 49 must exert in order to close off the middle of the primary tubing completely. Therefore, a lever 43 with a larger ratio can be used to enhance the force from the inflated diaphragm 46, so the device can be made smaller.

External valve 23 may be attached to the primary line at a head height differential, or distance from the top of the secondary fluid sufficient to provide sufficient hydrostatic pressure to close the valve 30 (see, e.g., FIG. 14C). For example, this height differential may be 15 inches.

Diaphragm 46 may be a silicone diaphragm 46 that sits inside the diaphragm housing 44. A metal pin 42 may be provided within a hole 41 to hold the pivot point of the lever 43. The primary line valve of FIG. 16 is configured to shut off flow of primary fluid during secondary infusion.

Various components that may be used to form secondary line valve 31 of FIG. 15 will now be described in connection with FIGS. 17A-20B, 25 and 26. Various combinations of these and/or other components for secondary line valve 31 are described in connection with FIGS. 21-26.

Figure 17A:
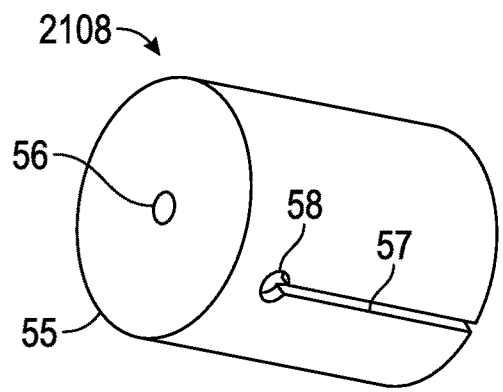
FIG. 17A is a schematic perspective front view of a priming dust cap for an external valve, according to certain aspects of the disclosure.
Figure 17B:
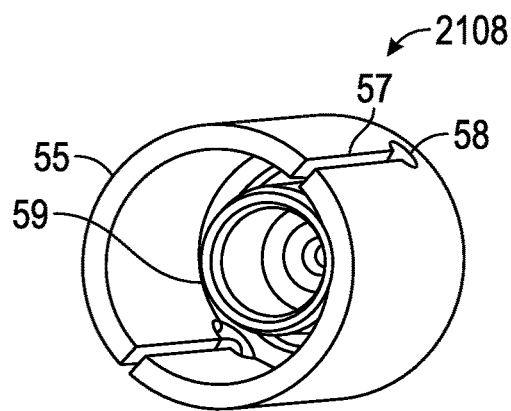
FIG. 17B is a schematic perspective rear view of a priming dust cap for an external valve, according to certain aspects of the disclosure.
Figure 17C:
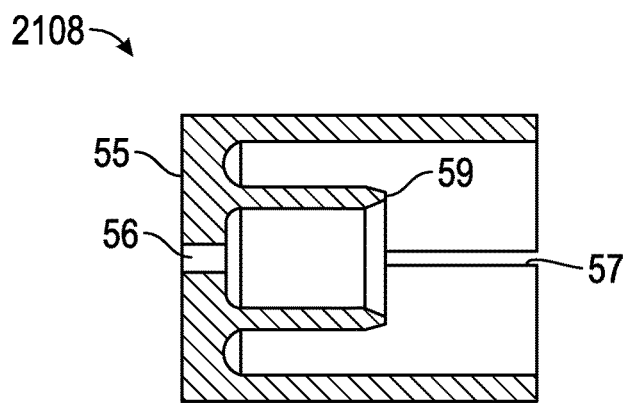
FIG. 17C is a schematic cross-sectional side view of a priming dust cap for an external valve, according to certain aspects of the disclosure.

Referring now to FIGS. 17A-17C, a cylindrical cap is shown containing an opening 56 through the exterior circular face 55 and an interior protrusion 59, along with two filleted stress-relieving cuts 57 and 58 on each side of the cap. The hollow cavity of the cap may be large enough to house the male end of a Luer connector such as a Texium® connector.

The interior protrusion 59 may be configured, for example, to fit into a male Luer such as a Texium® male Luer such that the Texium® male Luer opens when the interior protrusion 59 is completely pushed into the Texium® male Luer. The cap may be configured to remain pushed into the Texium® male Luer until it is physically pulled out by the user. This component may sometimes be referred to as the dust cap 2108. Dust cap 2108 may be disposed on an end of a needle-free connector such as a Texium® connector on the secondary line to allow for priming of the secondary line.

Figure 18A:
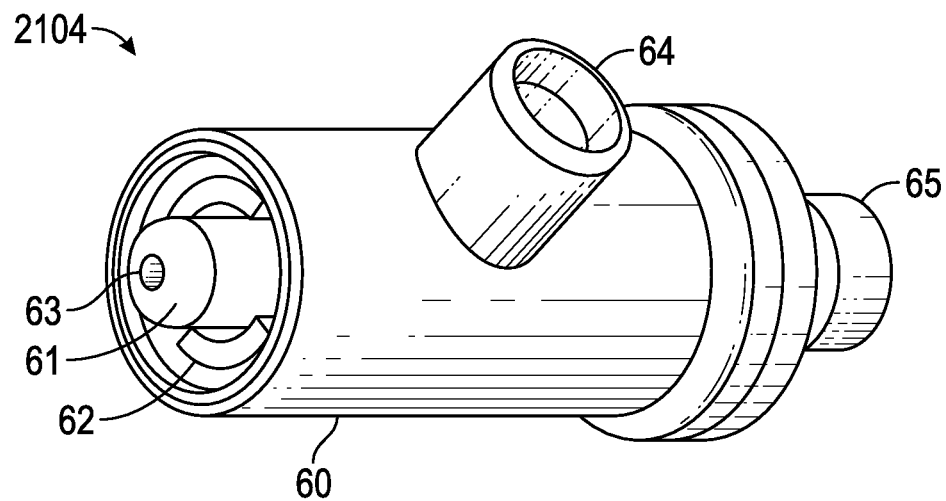
FIG. 18A is a schematic perspective view of a needle-free bypass valve for an external valve, according to certain aspects of the disclosure.
Figure 18B:
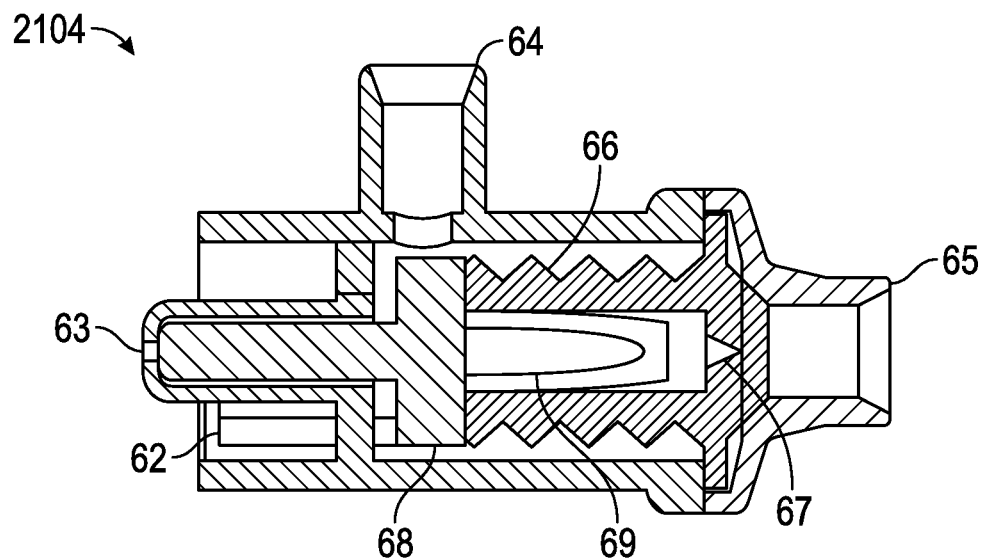
FIG. 18B is a schematic cross-sectional side view of a needle-free bypass valve for an external valve, according to certain aspects of the disclosure.

Referring now to FIGS. 18A and 18B, a needle-free bypass valve 2104 is shown. For example, needle-free bypass valve 2104 may be a Texium® male Luer with an additional open channel 64 protruding from the rounded exterior of the Texium® male Luer. This component may sometimes be referred to as the Texium® bypass 2104. As shown in FIG. 18B, needle-free bypass valve 2104 may include a flexible silicone part 66 that has a valve 67. When the needle-free bypass valve 2104 is connected to the Y-site 1208, the Y-site pushes the protrusions 62 back into the device 2104, which in turn pushes the plastic component 68 which pushes the plastic teeth 69 into the valve 67. This action opens the valve and allows the fluid such as the secondary fluid 1222 in secondary fluid line 1224 flowing into port 65 to pass through the device 2104 and flow out of port 63.

When the Texium® bypass is disconnected, valve 67 is closed and prevents fluid from flowing from port 65 out to port 63. However, the open channel 64 is located such that any fluid flowing through open channel 64 is directed toward opening 63 of the needle-free bypass valve 2104 and bypasses the valve 67 of the needle-free bypass valve 2104.

Referring now to FIGS. 19A and 19B, an embodiment of a lid valve 2102 is shown. As shown in FIG. 19A, lid valve 2102 may include a hinged body 81 containing an opening 83 through which infusion tubing 82 (e.g., secondary line 1224) can be fed. In the example of FIG. 19A, a lid 80 with a cam-shaped knob 84 is attached to the hinged body 81 such that the lid 80 can rotate axially about the hinge 85. A wedge 86 may be positioned between the infusion tubing 82 and the cam-shaped knob 84. As shown in FIG. 19A, when the lid 80 is down or closed and resting on the hinged body 81, the radius of the cam-shaped knob 84 is such that it does not push the wedge 86 into the infusion tubing 82 and the lid valve is in an open position through which fluid can flow. As shown in FIG. 19B, when the lid 80 is up and away from the hinged body 81, the radius of the cam-shaped knob 84 is such that it pushes the wedge 86 directly and completely into the infusion tubing 82 to close tubing 82 and prevent flow therethrough. Lid valve 2102 may be used to close off the secondary line until the primary line is clamped into the primary line valve.

Referring now to FIGS. 20A and 20B, an embodiment of a priming valve 2107 is shown. As shown in FIG. 20A, priming valve 2107 may include an entry channel 91 leading into a main cavity 90 and an opening 89 leading out of the main cavity 90 and into a separate cavity 95. A button 97 extends through an opening 99 at the top of the main cavity 90, and the top of the button 97 is covered with a water-tight and flexible membrane 96. The button 97 is connected to a shaft 98 which interacts with a plunger 92 loaded by a spring 93, which are both housed in the separate cavity 95. As shown in FIG. 20B, when the button 97 is depressed, the button shaft 98 pushes the plunger 92 into the spring 93, which exposes opening 89 and directs fluid from the main cavity 90 to flow out through an exit channel 94 via the separate cavity 95. As shown in FIG. 20A, when the button is released, or in its relaxed state, the plunger 92 is pushed against opening 89 by the force of spring 93, which blocks any flow of fluid out of the main cavity 90. Conversely, when button 97 is compressed, fluid may also enter through channel 94 and exit through channel 91 via the same mechanism described if desired. Priming valve 2107 may be configured to open the secondary line to allow forward and backpriming of the secondary line.

Figure 21:
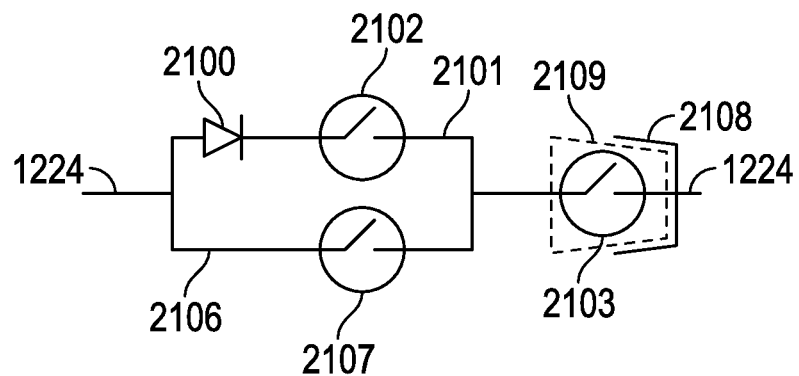
FIG. 21 is a schematic diagram of a dual branch secondary line valve of an external valve, according to certain aspects of the disclosure.

As noted above, FIGS. 21, 22, 23, and 24 each show an exemplary configuration of secondary line valve 31. Referring now to FIG. 21, a dual-branch secondary valve 31 is shown in which a check valve 2100 and a lid valve 2102 are provided on a first branch 2101 of secondary line 1224, and a priming valve 2107 is provided on a second, parallel branch 2106. A needle free male Luer such as a Texium® male Luer 2109 may also be provided with a dust cap 2108 and enclosing the valve 2103 therein. The Texium® male Luer 2109 with dust cap 2108 may be connected to a Y-site 1208 on the primary line.

Still referring to FIG. 21, the dust cap 2108 may be depressed by a nurse or other caregiver to open the valve 2103, thereby allowing flow through secondary line 1224 and through the dust cap opening 56. In order to back prime the secondary line, the secondary bag 1220 may be lowered and the priming button of priming valve 2107 may be depressed to open the priming valve 2107, which allows primary fluid to flow up the bottom branch 2106. In this way, back priming of the secondary line may be performed through the bottom branch 2106. Forward priming may be performed when valve 2103 is not connected to Y-site 1208. For example, while valve 2103 is not connected to Y-site 1208, the priming button of valve 2107 may be depressed to open the priming valve 2107 and dust cap 2108 may be (e.g., concurrently) depressed to release air in the line through the opening 56. In this way, controlled secondary fluid flow, up to the Texium® valve 307 may be allowed (e.g., without leaking) for forward priming the secondary line. When the Texium® male bier 2109 is connected to the Y-site 1208 and the lid valve 2102 is opened, the secondary fluid will flow through the open top branch 2101 via the open lid valve 2102 and the open Texium® valve 2103. The check valve 2100 ensures that secondary fluid only flows in the forward direction towards the Y-site 1208.

Figure 22:
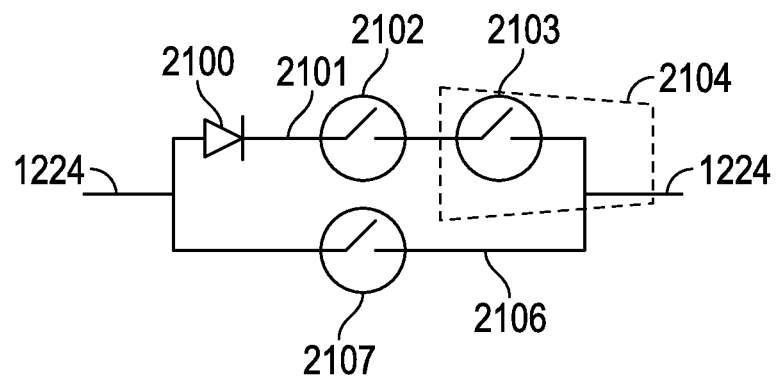
FIG. 22 is a schematic diagram of another dual branch secondary line valve of an external valve, according to certain aspects of the disclosure.

Referring now to FIG. 22, another embodiment of a dual-branch secondary valve implementation for valve 31 is shown which includes a check valve 2100, a lid valve 2102, and a needle-free valve such as a Texium® valve 2103 on the top branch 2101, and a priming valve 2107 on the bottom branch 2106. A needle-free bypass valve 2104 may be used that encloses valve 2103 and, via the bypass therein, merges the top branch 2101 with the bottom branch 2106. The needle-free bypass valve 2104 connects to the Y-site 1208 on the primary line.

Still referring to FIG. 22, the needle-free bypass valve 2104 allows for priming to occur without connection to the Y-site 1208 on the primary line. When the priming button for valve 2107 is depressed, the secondary fluid will flow to the tip of the needle-free bypass valve 2104, because the priming valve 2107 will be open allowing fluid to flow through the branch 2106. Connection to the Y-site 1208 by the Texium® valve and the closing of the lid opens the lid valve 2102 and the needle-free bypass valve 2104 which causes forward fluid flow through the check valve 2100 as desired. The check valve 2100 ensures that fluid will only flow in the forward direction.

Figure 23:
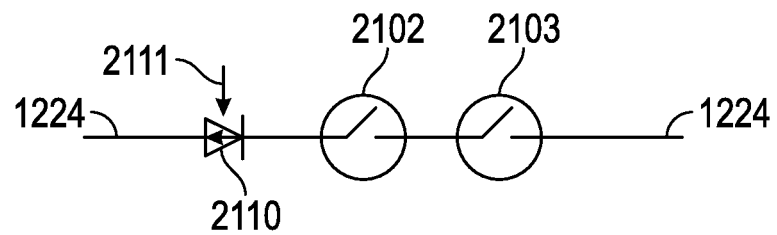
FIG. 23 is a schematic diagram of a single branch secondary line valve of an external valve, according to certain aspects of the disclosure.
Figure 24:
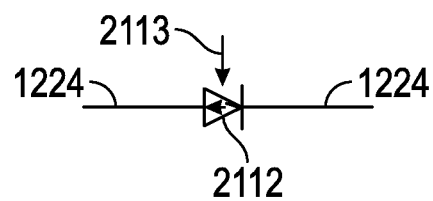
FIG. 24 is a schematic diagram of another single branch secondary line valve of an external valve, according to certain aspects of the disclosure.

Referring now to FIG. 23, a single branch secondary valve implementation for secondary valve 31 is shown. In the single branch implementation of FIG. 23, valve 31 includes a disengaging check valve 2110 with disengaging button 2111, a lid valve 2102, and connector 2103. The connector 2103 connects to the Y-site 1208 on the primary line, and may have needle-free fluid coupling functionality.

Still referring to FIG. 23, the disengaging button 2111 allows for forward and backward priming by opening the disengaging check valve 2110 when the button 2111 is depressed. Connector 2103 may have similar construction and components to a Texium® valve and is closed when not connected to the Y-site 1208. When the lid is closed to open lid valve 2102, and the connector 2103 is connected at the Y-site 1208, the lid valve 2102 and the connector valve 2103 are open and the secondary fluid will flow therethrough. The disengaging check valve 2110 allows fluid to only flow in the forward direction when button 11 is released.

Referring now to FIG. 4, another implementation of a single branch secondary valve for valve 31 is shown, which includes only a disengaging check valve 2112 having a suitable cracking pressure. Valve 2112, may include a disengaging button 2113 that, when compressed, allows for forward and backward priming by opening the valve 2112 when the button is depressed. Valve 2112 allows fluid to only flow in the forward direction when button 2113 is not depressed, and allows fluid to flow in both directions when the button 2113 is depressed. Further, valve 2112 has a breaking pressure or cracking pressure required to get fluid to flow in the forward direction. A valve of this type may use the breaking pressure of the valve to serve the purpose of the needle-free valve (e.g., Texium® valve) features described above in connection with the embodiments of FIGS. 21, 22, and 23. For example, fluid will only flow through valve 2112 when the cracking pressure of the valve 2112 is overcome by, for example, a suction force created by the pump 1212.

Figure 25:
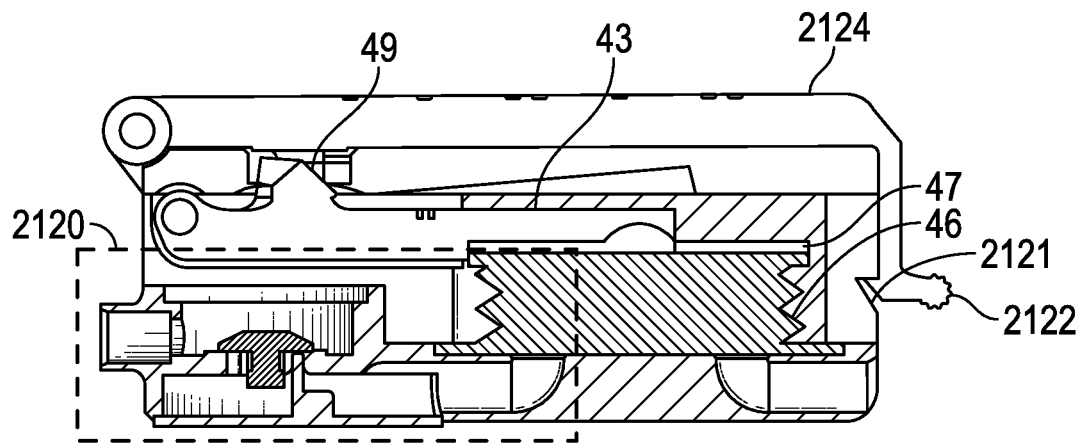
FIG. 25 is a cross-sectional view of an integrated external valve, according to certain aspects of the disclosure.

Referring now to FIG. 25, an integrated system is shown with a primary line valve and a secondary line valve therein. As in the example of FIG. 16, in the example of FIG. 25, the external valve includes diaphragm 46, pusher plate 47, lever arm 43, and wedge 49 on the lever arm 43. As shown in FIG. 25, a lid 2124 on the integrated device has a clasp 2122, which may be closed to secure the primary tubing within the external valve to help ensure that primary fluid is blocked in response to fluid in the secondary tubing. Lid 2124 may include a clasp 2122 with a protrusion 2121. Protrusion 2121 may be configured to engage with a corresponding recess in a housing for the valve as shown in FIG. 25 to latch and secure lid 2124 in a closed position. However, this is merely illustrative. In other embodiments, lid 2124 may have a recess that engages with a protrusion on the valve housing or other latching arrangements may be provided.

Figure 26:
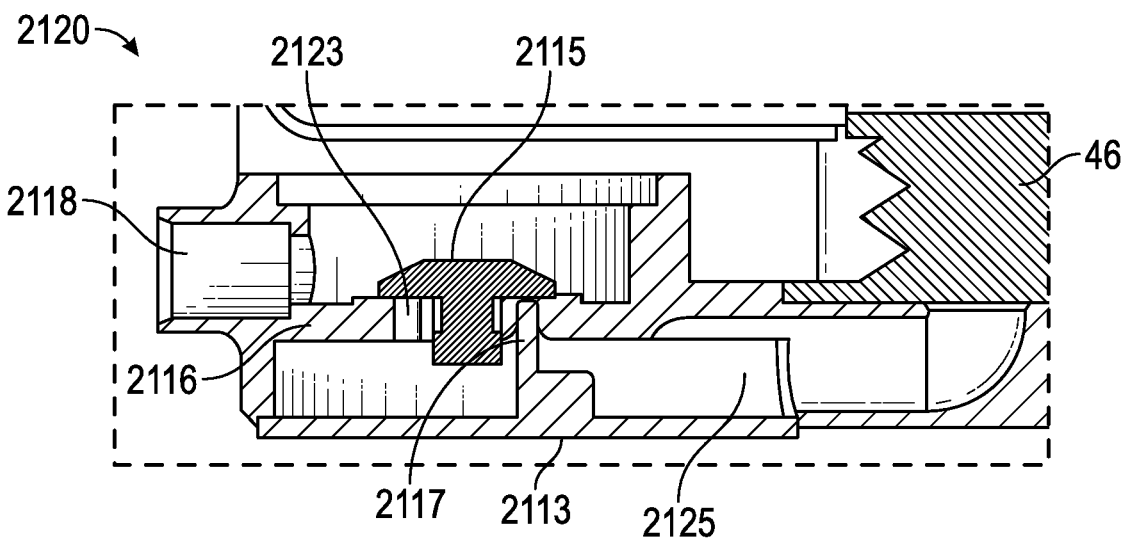
FIG. 26 is a zoomed in view of a secondary line valve and a diaphragm in the integrated external valve of FIG. 25, according to certain aspects of the disclosure.

A secondary line valve system 2120, indicated in FIG. 25, is detailed in FIG. 26. As shown in FIG. 26, secondary line valve system 2120 may allow secondary fluid flow from the diaphragm 46 and up to a disengageable check valve 2115 (e.g., an umbrella valve), which does not open until the cracking pressure of the disengageable check valve 2115 is overcome by the pump. The secondary line valve system 2120 shown in FIG. 26 may allow for forward and backward priming via a button.

Fluid from the diaphragm 46 may flow into a cavity 2125 below umbrella valve 2115. The umbrella valve 2115 may sit on a platform 2116. Platform 2116 may have a thickness configured to set a cracking pressure for the umbrella valve 2115. For example, a relatively thicker platform 2116 may generate a relatively higher cracking pressure for umbrella valve 2115. Umbrella valve 2115 may have a cracking pressure such that fluid in the cavity 2125 does not flow through umbrella valve 2115 and exit downstream through outlet 2118 unless the fluid is being pulled by a pump.

The hydrostatic pressure of the secondary fluid is not enough to overcome the cracking pressure of the umbrella valve 2115. The umbrella valve 2115 may be a unidirectional check valve, such that fluid is prevented from entering upstream through outlet 2118 and into cavity 2125. Umbrella valve 2115 can be manually disengaged via the priming button, which may consist of an external plate 2113 and a protuberance 2117 attached to the plate 2113. When the plate 2113 is depressed, the protuberance 2117 pushes up against the underside of umbrella valve 2115, lifting up the umbrella valve 2115 and allowing fluid to exit downstream through outlet 2118.

External plate 2113 may be flexible and resilient such that when the plate is released, it returns to its original position and the protuberance 2117 no longer displaces umbrella valve 2115, allowing umbrella valve 2115 to return to its fluid blocking state. For back priming of the secondary line, umbrella valve 2115 can be disengaged by pressing external plate 2113, thereby allowing fluid to enter upstream through outlet 2118 and into cavity 2125, where it subsequently continues upstream toward the drip chamber. As shown in FIGS. 25 and 26, lid 2124 may be substantially disposed on a first side of the external valve that is opposite to a second side on which the external plate 2113 is disposed.

The disclosed embodiments may provide a secondary infusion device that blocks the flow of the primary fluid during the secondary infusion and automatically regulates the flow of the secondary fluid during the infusion. The advantages of the present disclosure include, without limitation, a reduction of the number of steps required to set up a secondary infusion, thereby making secondary infusions more reliable, and further an elimination of the need for a check valve on every primary line, thereby making medical practice more cost-efficient. In various embodiments, a valve may include one valve system regulating primary fluid flow and one valve system regulating secondary fluid flow.

The subject technology is illustrated, for example, according to various aspects described above. Various examples of these aspects are described as numbered concepts or clauses (1, 2, 3, etc.) for convenience. These concepts or clauses are provided as examples and do not limit the subject technology. It is noted that any of the dependent concepts may be combined in any combination with each other or one or more other independent concepts, to form an independent concept. The following is a non-limiting summary of some concepts presented herein:

Concept 1. A valve, comprising:
first and second structures configured to be disposed on opposing sides of a first fluid line, wherein the first structure comprises a recess configured to receive the first fluid line;
at least one tab in the recess configured to partially compress the first fluid line; and
an actuating mechanism configured to be moved toward the first fluid line by a pressure from a fluid within a second fluid line.

Concept 2. The valve of Concept 1 or any other Concept, wherein the at least one tab comprises a first tab formed on a first side of the recess and a second tab formed on an opposing second side of the recess.

Concept 3. The valve of Concept 2 or any other Concept, wherein the first tab is disposed at a first location along the length of the recess and wherein the second tab is disposed at a second, different, location along the length of the recess.

Concept 4. A system comprising the valve of Concept 1 or any other Concept and the second fluid line, wherein the valve is coupled to the second fluid line and wherein the second fluid line comprises a check valve.

Concept 5. The system of Concept 4 or any other Concept, further comprising: the first fluid line disposed in the recess; a first fluid container coupled to the first fluid line; a second fluid container coupled to the second fluid line; and a pump configured to receive fluids from the first and second fluid lines via the valve.

Concept 6. The system of Concept 5 or any other Concept, wherein the first fluid container contains a first medical fluid and wherein the second fluid container contains a second, different, medical fluid.

Concept 7. The valve of Concept 1 or any other Concept, wherein the actuating mechanism comprises:
a diaphragm having a surface configured to contact the fluid in a portion of the second fluid line; and
a pin extending from the diaphragm to the first fluid line, wherein the pin has a surface configured to contact a portion of the first fluid line, and wherein the diaphragm surface is larger than the pin surface.

Concept 8. A valve, comprising:
at least one structure having a recess configured to receive a first fluid line containing a first fluid; and
an actuating mechanism configured to be moved toward the first fluid line by a pressure from a second fluid in a second fluid line, wherein the actuating mechanism comprises: a diaphragm having a surface configured to contact the second fluid in a portion of the second fluid line; and
a pin extending from the diaphragm to the first fluid line, wherein the pin has a surface configured to contact a portion of the first fluid line, and wherein the surface of the diaphragm is larger than the surface of the pin.

Concept 9. The valve of Concept 8 or any other Concept, wherein the pressure from the second fluid in the second fluid line is generated by a hydrostatic pressure on the diaphragm from the second fluid in the second fluid line when a first fluid container coupled to the first fluid line is disposed at a common height with a second fluid container coupled to the second fluid line.

Concept 10. The valve of Concept 9 or any other Concept, wherein the first fluid container comprises a first intravenous fluid bag containing a first medical fluid and wherein the second fluid container comprises a second intravenous fluid bag containing a second, different, medical fluid Concept 11. The valve of Concept 8 or any other Concept, further comprising a plurality of protrusions in the recess configured to crimp the first fluid line.

Concept 12. The valve of Concept 11 or any other Concept, wherein a portion of the first fluid line that is crimped is disposed at least partially between first and second protrusions of the plurality of protrusions.

Concept 13. The valve of Concept 8 or any other Concept, wherein the at least one structure comprises first and second structures configured to be snapped onto the first fluid line.

Concept 14. A system comprising the valve of Concept 8 or any other Concept, the system further comprising:
a support structure;
first and second containers attached at a common height to the support structure;
first and second drip chambers coupled respectively between the first and second containers and the first and second fluid lines;
a check valve in the second fluid line; and
a pump configured to receive a first fluid from the first fluid line or a second fluid from second fluid line based on a position of the actuating mechanism of the valve.

Concept 15. A method, comprising:
providing a first fluid container coupled to a first fluid line;
providing a second fluid container coupled to a second fluid line having an external valve with an actuating member;
attaching the external valve to the first fluid line; and closing the first fluid line by moving the actuating member in a first direction using a hydrostatic pressure of a fluid in the second fluid line.

Concept 16. The method of Concept 15 or any other Concept, wherein providing the first fluid container and providing the second fluid container comprise providing the first and second fluid containers at a common height above the external valve.

Concept 17. The method of Concept 16 or any other Concept, further comprising opening the first fluid line by moving the actuating member in an opposing second direction using a hydrostatic pressure in the first fluid line when the hydrostatic pressure of the fluid in the second fluid line falls due to emptying of the second fluid container.

Concept 18. The method of Concept 17 or any other Concept, further comprising opening a check valve in the second fluid line to back prime the second fluid line.

Concept 19. The method of Concept 15 or any other Concept, wherein attaching the external valve to the first fluid line comprises crimping the first fluid line by partially compressing portions of the first fluid line with a plurality of tabs disposed in a recess in the external valve.

Concept 20. A method of testing a medical fluid infusion system, the method comprising:
   coupling a first fluid tube to an infusion pump;
   coupling a second fluid tube having a check valve to the infusion pump;
   attaching an external valve of the second fluid tube to the first fluid tube;
   attaching a first container coupled to the first fluid tube to a support structure at a height above the external valve;
   attaching a second container coupled to the second fluid tube to the support structure at the same height above the external valve;
   reversing a flow of a first fluid in the first fluid tube with the infusion pump; and
   determining whether the external valve is properly attached to the first fluid tube by monitoring a pressure in the first fluid tube while reversing the flow.

Concept 21. The method of Concept 20 or any other Concept, wherein a portion of the external valve forms a portion of the second fluid tube, and wherein the portion of the external valve includes a diaphragm of an actuating member of the external valve that is disposed in contact with a fluid in the second fluid tube.

Concept 22. A valve, comprising:
   a primary line valve having an actuating mechanism configured to be moved toward a first fluid line by a pressure from a fluid within a second fluid line; and a secondary line valve having at least one valving component operable to open the secondary line valve for priming of the fluid in the second fluid line.

Concept 23. The valve of Concept 22 or any other Concept, wherein the at least one valving component comprises:
   a check valve and a lid valve in series on a first branch of the secondary line
   a priming valve on a parallel second branch of the secondary line valve;
   a needle-free valve coupled to the first and second branches; and
   a dust cap disposed on the needle-free valve.

Concept 24. The valve of Concept 22 or any other Concept, wherein the at least one valving component comprises:
   a check valve, a lid valve, and a needle-free valve in series on a first branch of the secondary line valve; and
   a priming valve on a parallel second branch of the secondary line valve, wherein the needle-free valve comprises a bypass that couples the first branch and the parallel second branch.

Concept 25. The valve of Concept 22 or any other Concept, wherein the at least one valving component comprises a disengageable check valve, a lid valve, and a needle-free valve in series.

Concept 26. The valve of Concept 22 or any other Concept, wherein the at least one valving component comprises a disengageable check valve having a cracking pressure for forward flow of fluid therethrough.

Concept 27. The valve of Concept 22 or any other Concept, wherein the primary line valve includes at least one feature configured to partially compress the first fluid line in the absence of the pressure from the fluid within the second fluid line.

Concept 28. A system comprising the valve of Concept 22 or any other Concept, the system further comprising:
   the first fluid line;
   a first fluid container coupled to the first fluid line;
   a second fluid container coupled to the second fluid line; and
   a pump configured to receive fluids from the first and second fluid lines via the valve.

Concept 29. The system of Concept 28 or any other Concept, wherein the first fluid container contains a first medical fluid and wherein the second fluid container contains a second, different, medical fluid.

Concept 30. The system of Concept 29 or any other Concept, the system further comprising:
   a support structure; and
   the first and second fluid containers attached at a common height to the support structure.

Concept 31. A method, comprising:
   providing a first fluid container coupled to a first fluid line;
   providing a second fluid container coupled to a second fluid line having an external valve with an actuating member;
   priming a second fluid in the second fluid line at least in part v operating a portion of the external valve;
   attaching the external valve to the first fluid line; and
   closing the first fluid line by moving the actuating member in a first direction using a hydrostatic pressure of a fluid in the second fluid line.

Concept 32. The method of Concept 31 or any other Concept, wherein the priming comprises operating an umbrella valve within the external valve by compressing a button formed at least in part from an external plate of the external valve.

Concept 33. The method of Concept 32 or any other Concept, wherein the attaching comprises closing a lid of the external valve to secure a portion of the first fluid line within the external valve, wherein the lid is disposed on a first side of the external valve and wherein the external plate is disposed on an opposing second side of the external valve.

The previous description is provided to enable a person of ordinary skill in the art to practice the various aspects described herein. While the foregoing has described what are considered to be the best mode and/or other examples, it is understood that various modifications to these aspects will be readily apparent to those skilled in the art, and the generic principles defined herein may be applied to other aspects. Thus, the claims are not intended to be limited to the aspects shown herein, but is to be accorded the full scope consistent with the language claims, wherein reference to an element in the singular is not intended to mean "one and only one"

unless specifically so stated, but rather "one or more." Unless specifically stated otherwise, the terms "a set" and "some" refer to one or more. Pronouns in the masculine (e.g., his) include the feminine and neuter gender (e.g., her and its) and vice versa. Headings and subheadings, if any, are used for convenience only and do not limit the invention.

It is understood that the specific order or hierarchy of steps in the processes disclosed is an illustration of exemplary approaches. Based upon design preferences, it is understood that the specific order or hierarchy of steps in the processes may be rearranged and some steps may be omitted. Some of the steps may be performed simultaneously. The accompanying method claims present elements of the various steps in a sample order, and are not meant to be limited to the specific order or hierarchy presented.

Terms such as "top," "bottom," "front," "rear" and the like as used in this disclosure should be understood as referring to an arbitrary frame of reference, rather than to the ordinary gravitational frame of reference. Thus, a top surface, a bottom surface, a front surface, and a rear surface may extend upwardly, downwardly, diagonally, or horizontally in a gravitational frame of reference.

A phrase such as an "aspect" does not imply that such aspect is essential to the subject technology or that such aspect applies to all configurations of the subject technology. A disclosure relating to an aspect may apply to all configurations, or one or more configurations. A phrase such as an aspect may refer to one or more aspects and vice versa. A phrase such as an "embodiment" does not imply that such embodiment is essential to the subject technology or that such embodiment applies to all configurations of the subject technology. A disclosure relating to an embodiment may apply to all embodiments, or one or more embodiments. A phrase such an embodiment may refer to one or more embodiments and vice versa.

The word "exemplary" is used herein to mean "serving as an example or illustration." Any aspect or design described herein as "exemplary" is not necessarily to be construed as preferred or advantageous over other aspects or designs.

All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112, sixth paragraph, unless the element is expressly recited using the phrase "means for" or, in the case of a method claim, the element is recited using the phrase "step for." Furthermore, to the extent that the term "include," "have," or the like is used in the description or the claims, such term is intended to be inclusive in a manner similar to the term "comprise" as "comprise" is interpreted when employed as a transitional word in a claim.

What is claimed is:

1. A valve, comprising:
   first and second structures configured to be disposed on opposing sides of a first fluid line, wherein the first structure comprises a recess configured to receive the first fluid line;
   at least one tab in the recess configured to partially compress the first fluid line; and
   an actuating mechanism configured to be moved toward the first fluid line by a pressure from a fluid within a second fluid line.

2. The valve of claim 1, wherein the at least one tab comprises a first tab formed on a first side of the recess and a second tab formed on an opposing second side of the recess.

3. The valve of claim 2, wherein the first tab is disposed at a first location along a length of the recess and wherein the second tab is disposed at a second, different, location along the length of the recess.

4. A system comprising the valve of claim 1 and the second fluid line, wherein the valve is coupled to the second fluid line and wherein the second fluid line comprises a check valve.

5. The system of claim 4, further comprising:
   the first fluid line disposed in the recess;
   a first fluid container coupled to the first fluid line;
   a second fluid container coupled to the second fluid line; and
   a pump configured to receive fluids from the first and second fluid lines via the valve.

6. The system of claim 5, wherein the first fluid container contains a first medical fluid and wherein the second fluid container contains a second, different, medical fluid.

7. The valve of claim 1, wherein the actuating mechanism comprises:
   a diaphragm having a surface configured to contact the fluid in a portion of the second fluid line; and
   a pin extending from the diaphragm to the first fluid line, wherein the pin has a surface configured to contact a portion of the first fluid line, and wherein the diaphragm surface is larger than the pin surface.

* * * * *